US008304600B2

(12) United States Patent
Noda et al.

(10) Patent No.: US 8,304,600 B2
(45) Date of Patent: Nov. 6, 2012

(54) ABSORBENT ARTICLE

(75) Inventors: Yuki Noda, Kagawa (JP); Kenichiro Kuroda, Kagawa (JP); Kumiko Nishikawa, Kagawa (JP); Satoshi Mizutani, Kagawa (JP); Hideyuki Ishikawa, Kagawa (JP); Akihiro Kimura, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 740 days.

(21) Appl. No.: 11/766,867

(22) Filed: Jun. 22, 2007

(65) Prior Publication Data
US 2008/0045915 A1    Feb. 21, 2008

(30) Foreign Application Priority Data

Jun. 23, 2006 (JP) ................................. 2006-174505
Jun. 22, 2007 (JP) ................................. 2007-164511

(51) Int. Cl.
*A61F 13/15* (2006.01)
*A61F 13/20* (2006.01)

(52) U.S. Cl. ......... 604/384; 428/167; 428/170; 428/179

(58) Field of Classification Search .................. 428/167, 428/170–172, 175, 179, 181–184; 604/378–380, 604/384
See application file for complete search history.

(56) References Cited

U.S. PATENT DOCUMENTS

| | | | |
|---|---|---|---|
| 2,596,292 A | 5/1952 | Sackner | |
| 3,458,905 A | 8/1969 | Dodson, Jr. et al. | |
| 3,485,706 A | 12/1969 | Evans | |
| 3,486,168 A | 12/1969 | Evans et al. | |
| 3,766,922 A * | 10/1973 | Krusko | 604/374 |
| 4,016,317 A | 4/1977 | Kalwaites | |
| 4,016,319 A | 4/1977 | Marshall | |
| 4,038,452 A | 7/1977 | Kobayashi et al. | |
| 4,186,463 A * | 2/1980 | Marshall | 19/304 |
| 4,190,695 A | 2/1980 | Niederhauser | |
| 4,379,799 A * | 4/1983 | Holmes et al. | 428/131 |
| 4,582,666 A | 4/1986 | Kenworthy et al. | |
| 4,612,226 A | 9/1986 | Kennette et al. | |
| 4,695,500 A * | 9/1987 | Dyer et al. | 428/134 |

(Continued)

FOREIGN PATENT DOCUMENTS

CN       1294904       5/2001

(Continued)

OTHER PUBLICATIONS

Office Action issued to U.S. Appl. No. 11/762,421, mailed Oct. 6, 2009.

(Continued)

*Primary Examiner* — Melanie Hand
(74) *Attorney, Agent, or Firm* — Lowe, Hauptman, Ham & Berner, LLP

(57) ABSTRACT

An absorbent article comprising nonwoven fabric having convex and concave surfaces, and that allows liquid such as excreta and the like to permeate quickly. A sanitary napkin has a plurality of raised ridge portions and groove portions in a top sheet member. The fiber density of the side edge portions of each of the plurality of raised ridge portions in the thickness direction of the nonwoven fabric is substantially uniform, and is higher than the average fiber density in the raised ridge portions. The fiber density of the central portion between both the side edge portions of each of the plurality of raised ridge portions is substantially uniform in the thickness direction of the nonwoven fabric, and is lower than the average fiber density in the raised ridge portions.

20 Claims, 14 Drawing Sheets

U.S. PATENT DOCUMENTS

| | | | |
|---|---|---|---|
| 4,735,842 A | 4/1988 | Buyofsky et al. | |
| 4,787,947 A | 11/1988 | Mays | |
| 4,835,042 A | 5/1989 | Dohzono et al. | |
| 4,840,829 A | 6/1989 | Suzuki et al. | |
| 5,607,414 A | 3/1997 | Richards et al. | |
| 5,613,962 A | 3/1997 | Kenmochi et al. | |
| 5,618,610 A * | 4/1997 | Tomita et al. | 428/152 |
| 5,733,625 A | 3/1998 | Tsuchiya et al. | |
| 5,897,547 A | 4/1999 | Schmitz | |
| 5,900,109 A | 5/1999 | Sanders et al. | |
| 6,039,555 A | 3/2000 | Tsuji et al. | |
| 6,096,016 A * | 8/2000 | Tsuji et al. | 604/378 |
| 6,395,957 B1 | 5/2002 | Chen et al. | |
| 6,451,718 B1 * | 9/2002 | Yamada et al. | 442/149 |
| 6,582,798 B2 | 6/2003 | Thomas | |
| 6,586,076 B1 | 7/2003 | Mizutani et al. | |
| 6,610,173 B1 | 8/2003 | Lindsay et al. | |
| 6,641,902 B1 | 11/2003 | Kobayashi et al. | |
| 6,802,932 B2 | 10/2004 | Kudo et al. | |
| 6,818,802 B2 | 11/2004 | Takai et al. | |
| 6,855,424 B1 | 2/2005 | Thomas et al. | |
| 6,867,156 B1 | 3/2005 | White et al. | |
| 6,936,333 B2 | 8/2005 | Shizuno et al. | |
| 7,507,463 B2 | 3/2009 | Noda et al. | |
| 7,553,535 B2 | 6/2009 | Noda et al. | |
| 7,662,462 B2 | 2/2010 | Noda et al. | |
| 2002/0010449 A1 | 1/2002 | Mizutani | |
| 2003/0198784 A1 | 10/2003 | Mizutani et al. | |
| 2003/0232558 A1 | 12/2003 | Moody, III et al. | |
| 2004/0204697 A1 | 10/2004 | Litvay | |
| 2005/0177121 A1 | 8/2005 | Mizutani et al. | |
| 2008/0289157 A1 | 11/2008 | Higashinaka et al. | |

FOREIGN PATENT DOCUMENTS

| | | | |
|---|---|---|---|
| DE | 4437165 | A1 | 4/1996 |
| DE | 102005036759 | A1 | 8/2006 |
| EP | 0703308 | | 3/1996 |
| EP | 0903136 | A2 | 3/1999 |
| EP | 0926287 | A1 | 6/1999 |
| EP | 1090615 | | 4/2001 |
| EP | 1201213 | A2 | 5/2002 |
| EP | 1269956 | | 1/2003 |
| JP | S56-119249 | A | 9/1981 |
| JP | 02-169718 | A | 6/1990 |
| JP | 02-229255 | A | 9/1990 |
| JP | 03-137257 | | 6/1991 |
| JP | H-04-221556 | A | 8/1992 |
| JP | 08-60509 | A | 3/1996 |
| JP | 08-216310 | A | 8/1996 |
| JP | H-08-302555 | A | 11/1996 |
| JP | 10-137291 | A | 5/1998 |
| JP | 2001-340382 | A | 12/2001 |
| JP | 2002-030557 | A | 1/2002 |
| JP | 2002-136547 | A | 5/2002 |
| JP | 2002243965 | | 8/2002 |
| JP | 2002-249965 | A | 9/2002 |
| JP | 2003126147 | | 5/2003 |
| JP | 3587831 | | 8/2004 |
| JP | 3587831 | B2 | 8/2004 |
| JP | 2007-175515 | A | 7/2007 |
| WO | 2005122817 | A1 | 12/2005 |

OTHER PUBLICATIONS

International Search Report of PCT/JP2007/061601 issued Aug. 7, 2007.
International Search Report of PCT/JP2007/060543 issued Jul. 10, 2007.
International Search Report of PCT/JP2007/061444 issued on Aug. 7, 2007.
Office Action issued to U.S. Appl. No. 11/755,376, mailed Jun. 30, 2009.
International Search Report of PCT/JP2007/061445 issued Jul. 31, 2007.
Office Action issued Aug. 4, 2009, from U.S. Appl. No. 11/748,712, filed May 15, 2007.
European Search Report for Application No. EP07743982, mailed Apr. 8, 2010.
Office Action issued to U.S. Appl. No. 11/748,712, mailed Mar. 23, 2010.
Office Action issued to CN Application No. 200780022784.6 mailed May 12, 2010.
Office Action issued to U.S. Appl. No. 11/762,421 mailed May 11, 2010.
Notice of Allowance Issued to U.S. Appl. No. 11/755,376, mailed Jun. 21, 2010.
Office Action Issued to U.S. Appl. No. 11/748,186, mailed Jun. 22, 2010.
Office Action issued to U.S. Appl. No. 12/511,115, mailed Sep. 14, 2010.
European Search Report for European Patent Application No. 07743977.6 issued Apr. 18, 2011.
European Search Report for European Patent Application No. 07743978.4 issued Apr. 18, 2011.
European Search Report for European Patent Application No. 07743979.2 issued Apr. 18, 2011.
European Search Report for European Patent Application No. 07744787.8 issued Apr. 29, 2011.
European Search Report for European Patent Application No. 07743980.0 issued Apr. 18, 2011.
European Search Report for European Patent Application No. 07743981.8 issued Apr. 18, 2011.
European Search Report for European Patent Application No. 07744921.3 issued Apr. 18, 2011.
European Search Report for European Patent Application No. 07744788.6 issued Apr. 29, 2011.
European Search Report for European Patent Application No. 07767438.0 issued Apr. 29, 2011.
Office Action issued to ID Application No. W00200804035 mailed Apr. 26, 2011.
Office Action issued to U.S. Appl. No. 11/748,712, mailed Mar. 29, 2012.
Japanese Office Action mailed Nov. 22, 2011 in corresponding Japanese Patent Application No. 2006-270111.
OA for U.S. Appl. No. 11/762,349 dated Oct. 25, 2011.

* cited by examiner

FIG. 13

| | | | | ave |
|---|---|---|---|---|
| EMBODIMENT (SANITARY NAPKINS FOR EVALUATION) | FIRST TIME (95ml/min 3ml) | INFILTRATION SPEED | sec | 4.3 |
| | | DRYING SPEED | sec | 7.0 |
| | | SPREADING AREA | mm2 | 404 |
| | | Qmax | °C·sec-1 | 0.12 |
| | SECOND TIME (95ml/min +4ml) | INFILTRATION SPEED | sec | 6.7 |
| | | DRYING SPEED | sec | 22.0 |
| | | SPREADING AREA | mm2 | 816 |
| | | Qmax | °C·sec-1 | 0.17 |
| | THIRD TIME (95ml/min +3ml) | INFILTRATION SPEED | sec | 7.4 |
| | | DRYING SPEED | sec | 45.0 |
| | | SPREADING AREA | mm2 | 960 |
| | | Qmax | °C·sec-1 | 0.19 |
| | REWETTING (SUPPRESSION PERFORMANCE OF LIQUID RETURN) | REWETTING AMOUNT | g | 0.27 |
| | | REWETTING RATE | % | 2.7 |
| FIRST COMPARISON (SANITARY NAPKINS FOR EVALUATION) | FIRST TIME (95ml/min 3ml) | INFILTRATION SPEED | sec | 7.9 |
| | | DRYING SPEED | sec | × |
| | | SPREADING AREA | mm2 | 504 |
| | | Qmax | °C·sec-1 | 0.50 |
| | SECOND TIME (95ml/min +4ml) | INFILTRATION SPEED | sec | 22.1 |
| | | DRYING SPEED | sec | × |
| | | SPREADING AREA | mm2 | 1000 |
| | | Qmax | °C·sec-1 | 0.46 |
| | THIRD TIME (95ml/min +3ml) | INFILTRATION SPEED | sec | 31.8 |
| | | DRYING SPEED | sec | × |
| | | SPREADING AREA | mm2 | 1100 |
| | | Qmax | °C·sec-1 | 0.52 |
| | REWETTING (SUPPRESSION PERFORMANCE OF LIQUID RETURN) | REWETTING AMOUNT | g | 2.94 |
| | | REWETTING RATE | % | 29.4 |
| SECOND COMPARISON (SANITARY NAPKINS FOR EVALUATION) | FIRST TIME (95ml/min 3ml) | INFILTRATION SPEED | sec | 4.7 |
| | | DRYING SPEED | sec | 25.0 |
| | | SPREADING AREA | mm2 | 960 |
| | | Qmax | °C·sec-1 | 0.11 |
| | SECOND TIME (95ml/min +4ml) | INFILTRATION SPEED | sec | 9.5 |
| | | DRYING SPEED | sec | 50.0 |
| | | SPREADING AREA | mm2 | 1400 |
| | | Qmax | °C·sec-1 | 0.22 |
| | THIRD TIME (95ml/min +3ml) | INFILTRATION SPEED | sec | 10.4 |
| | | DRYING SPEED | sec | × |
| | | SPREADING AREA | mm2 | 1560 |
| | | Qmax | °C·sec-1 | 0.45 |
| | REWETTING (SUPPRESSION PERFORMANCE OF LIQUID RETURN) | REWETTING AMOUNT | g | 2.73 |
| | | REWETTING RATE | % | 27.3 |
| REFERENCE: DEGREES OF PHYSICAL SENSATION FOR Qmax | 0 to 0.30 : SUBSTANTIALLY NOT COLD (DOES NOT FEEL WET) 0.30 to 0.50 : SLIGHTLY COLD (FEELS LIGHTLY WET) 0.50 and higher : COLD (FEELS SUBSTANTIALLY COLD) | | | |

ABSORBENT ARTICLE

This application is based on and claims the benefit of priority from Japanese Patent Application No. 2006-174505, filed on 23 Jun. 2006 and Japanese Patent Application No. 2007-164511, filed on 22 Jun. 2007, the content of which is incorporated herein by reference.

BACKGROUND OF THE INVENTION

1. Field of the Invention

The present invention relates to an absorbent article that uses nonwoven fabric.

2. Related Art

Conventionally, nonwoven fabrics are used in a wide range of fields from hygienic products such as baby diapers or feminine care articles (sanitary napkins) to cleaning products, such as wipers, or medical products, such as masks. Such nonwoven fabrics are used in many different fields, but when actually used in products of each of those fields, it is necessary that the nonwoven fabrics are manufactured with the properties and structures appropriate for their intended use.

Nonwoven fabric is fabricated by forming a fibrous layer (web) using a dry method or a wet method, and then bonding the fibers in a fibrous layer together using a chemical bonding method or a thermal bonding method. In processes that bond the fibers to compose the fibrous layer, there is a method in which a plurality of needles are repeatedly inserted into the fibrous layer, and a method in which physical force, such as a blowing race, is externally applied to the fibrous layer.

These methods however, only entangle the fibers and do not adjust the orientation or the arrangement of the fibers in the fibrous layer, or the shape of the fibrous layer. In other words, the fiber beds manufactured using these methods were simply sheet-shaped nonwoven fabrics.

Also, if a predetermined liquid of excreta is brought into contact with a nonwoven fabric used in a cover sheet, and the like, of an absorbent material, for example, a nonwoven fabric having an uneven surface is preferred in order to maintain or improve the feeling against the skin. (e.g. see Japanese Patent No. 3587831, hereinafter referred to as Patent Document 1)

The following information is disclosed in Patent Document 1. A plurality of fibrous layers, a first fibrous layer of a top layer, and a second fibrous layer of a bottom layer, composed of fabrics having different heat contraction characteristics are partially heat-bonded in predetermined patterns. The first fibrous layer partially bulges due to the heat contraction of the second fibrous layer.

When nonwoven fabrics, such as those described in Patent Document 1, are used as a surface sheet (top sheet) in a skin contact surface of an absorbent article, the following problems exist in the absorbent article relating to liquid infiltration performance and liquid return suppression performance.

An upper, first fibrous layer and a lower, second fibrous layer are heat-bonded in a predetermined pattern. The heat-bonded portion becomes a concave shape, and is substantially turned to film. An area occupancy rate of the heat-bonded portion is 11.5%. Menstrual blood that has migrated into the concave portion, that is the heat-bonded portion, becomes trapped there, and gradually travels into the top sheet from the adjacent non-heat-bonded portions. Therefore, when menstrual blood builds up in the concave portions, and if the wearer undergoes a change in their activity, there is the possibility that that menstrual blood will leak to the first fibrous layer surface of the surrounding the concave portions. Therefore, there is room to improve liquid infiltration performance.

The upper, first fibrous layer is partially bulged due to the heat contraction of the lower, second fibrous layer. The second fibrous layer is configured by a heat-contraction fiber with a high heat contraction rate, as such it coils due to heat-contraction. Therefore, the second fibrous layer heat-contracts and catches the surrounding fibers, so the second fibrous layer is in a state where there is a highly dense collection of fibers. This causes a highly dense region in the second fibrous layer to be formed at the backside of the top sheet. When this happens, menstrual blood, which should be absorbed, has difficulty in moving from the high-density region to an absorbent just below, and readily builds up in the high-density region. In other words, repeatedly excreted menstrual blood builds up in high-density regions of the backside of the top sheet, and takes an extremely long time to travel to the lower absorbent layer. Therefore, when the menstrual blood builds up at the backside of the top sheet, there is the possibility that the menstrual blood can leak to the first fiber layer surface if the wearer undergoes a changes in their activity. Therefore, there is room to improve liquid return suppression performance.

In this way, there is demand for an absorbent article with more comfortable performance, in which nonwoven fibers having concave portions and convex portion are used as a surface sheet (top sheet), which comes into contact with the skin. Particularly, this can help alleviate the problem of soiling the skin and causing the wearer to have a sticky feeling if menstrual blood is repeatedly excreted, or pressure is applied to contact the skin, such as in a sitting posture, and to improve liquid infiltration performance and liquid return suppression performance.

SUMMARY OF THE INVENTION

The present invention solves the aforementioned problems. An object of the present invention is to provide an absorbent article having nonwoven fabric including concavity and convexity in the surface, that is difficult to collapse by external pressure and the like, and that easily passes liquids, such as excreta and the like.

The inventors recognized that it is possible to manufacture nonwoven fabric that easily pass liquids, and have concave and raised ridge portions by moving fibers composing a fiber web, supported from a bottom surface side by a predetermined air-permeable supporting member, while blowing a gas from a top surface side, which lead to the completion of the invention.

According to a first aspect of the present invention, an absorbent article includes a first sheet member having a portion thereof that is partially liquid-permeable, a second sheet member that is liquid-impermeable, and an absorbent member disposed between the first and second sheet members, at least a portion of the first sheet member composes nonwoven fabric having a plurality of convex portions formed along a first direction on a first surface, and a plurality of concave portions oriented in a second direction perpendicular to the first direction in each of the plurality of convex portions on the first surface, formed to extend in the first direction, fiber density in a thickness direction of the nonwoven fabric of side edge areas of each of the plurality of convex portions is substantially uniform, and fiber density in the convex portions is higher than an average fiber density, and fiber density in a thickness direction of the nonwoven fabric of central areas, that are greater in height in the thickness direction than the side edge areas of each of the plurality of convex portions, is substantially uniform, and fiber density is lower than an average fiber density.

In a second aspect of the nonwoven fabric as described in the first aspect of the present invention, the nonwoven fabric includes first orientation fibers orientated along a first direction, and second orientation fibers orientated along a second direction, the side edge areas in each of the plurality of convex portions have more first orientation fibers compared to the central areas.

In a third aspect of the nonwoven fabric as described in the second aspect of the present invention, any concave portion of the plurality of concave portions is provided between adjacent a first convex portion and a second convex portion of the plurality of convex portions, includes a plurality of openings formed at predetermined intervals along the first direction, and linking portions positioned at the openings, linking the first convex portion and the second convex portion, the linking portion has more second orientation fibers compared to the side edge area.

In a fourth aspect of the nonwoven fabric as described in a third aspect of the present invention, portions surrounding each of the plurality of openings adjacent to the side edges have more first orientated fibers compared to that of the linking portions, and portions surrounding each of the plurality of openings adjacent to the linking portions have more second orientation fibers compared to that of the side edge areas.

In a fifth aspect of the nonwoven fabric as described in any one of the first to fourth aspects of the present invention, the central portions have more fibers obliquely orientated in a thickness direction compared to that of the side edge areas in each of the plurality of convex portions.

In a sixth aspect of the nonwoven fabric as described in any one of the first to fifth aspects of the present invention, the basis weight of fibers composing a bottom portion of each of the plurality of concave portions is lower compared to a basis weight of fibers composing the central portions in each of the plurality of convex portions.

In a seventh aspect of the nonwoven fabric as described in any one of the second to sixth aspects of the present invention, the fibers composing a bottom portion of each of the plurality of concave portions have more second orientation fibers compared to the fibers composing the central portions.

In an eighth aspect of the nonwoven fabric as described in any one of the first to seventh aspects of the present invention, the nonwoven fabric, one side thereof supported by a supporting member having portions allowing a fluid to pass therethrough, are formed with a plurality of convex portions and concave portions by a portion of the fibers of the fiber assembly being displaced by being blown by a fluid composed mainly of a gas.

According to the present invention, it is difficult to collapse by external pressure and the like, and the fiber density is controlled to prevent an extreme increase in density even if concave and convex portions are formed in order for easier permeation of a predetermined liquid such as excreta and the like and to improve liquid infiltration performance and liquid return suppression performance.

BRIEF DESCRIPTION OF THE DRAWINGS

FIG. 13 is a table displaying average evaluation results relating to the evaluation procedures.

DETAILED DESCRIPTION OF THE INVENTION

1. First Embodiment

Figure 1:
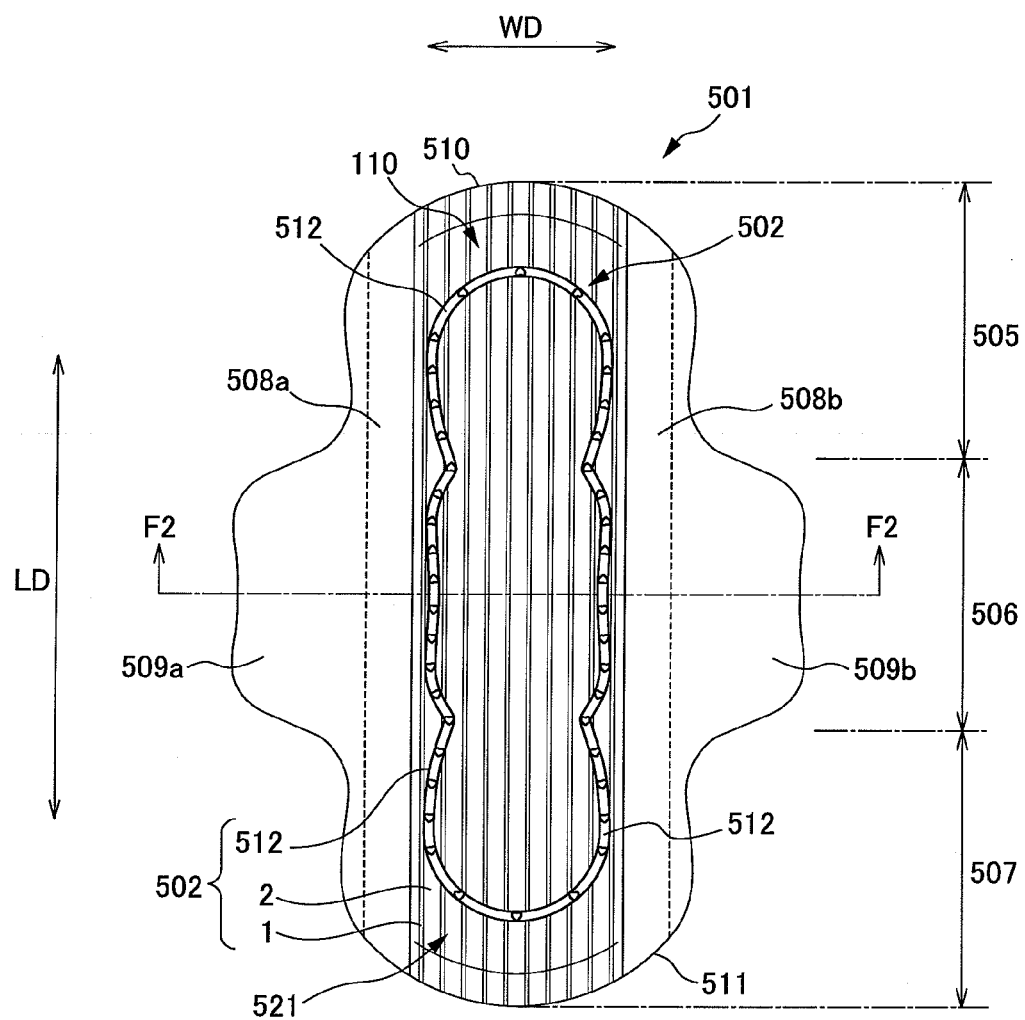
FIG. 1 is a plan view of a sanitary napkin according to a first embodiment of the present invention.
Figure 2:
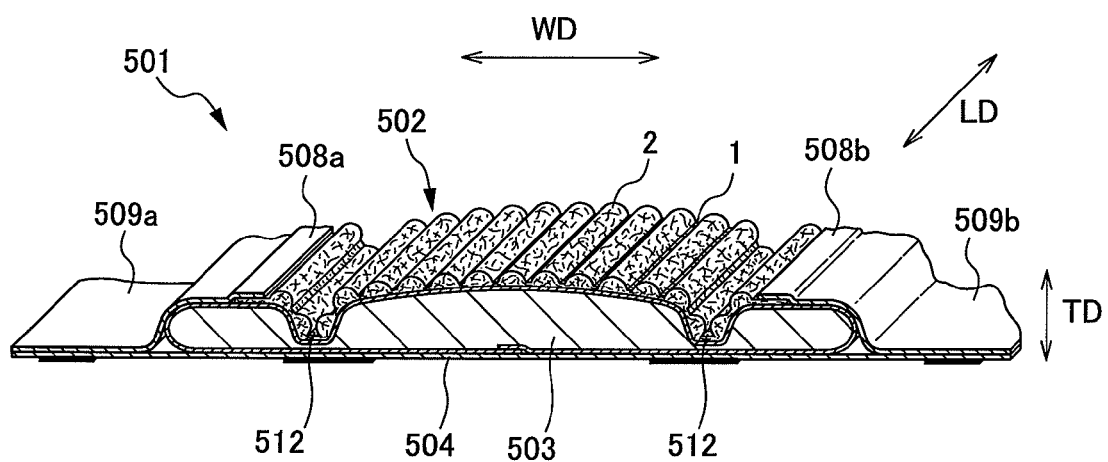
FIG. 2 is a sectional view along line F2-F2 as described in FIG. 1.

A sanitary napkin will now be used as an example to explain an absorbent article according to the present invention. FIG. 1 is a plan view of a sanitary napkin according to a first embodiment of the present invention. FIG. 2 is a sectional view along line F2-F2 as described in FIG. 1.

1-1. General Description

As shown in FIGS. 1 and 2, a sanitary napkin 501 as an absorbent article is provided with a liquid-permeable top sheet member 502; a liquid-impermeable back sheet member 504; and an absorbent body member 503 disposed between the top sheet member 502 and the back sheet member 504. In the longitudinal direction LD, the sanitary napkin 501 has a central portion 506 that includes an area that contacts makes contact with excretion organ; a front portion 505 that includes an area that makes contact with an anterior part of the body; and a back portion 507 that includes an area that makes contact with a posterior part of the body.

The sanitary napkin 501 is equipped with a pair of side sheets 508a, 508b along the longitudinal direction LD, on both side edges of the top sheet member 502. At least one of the side sheets 508a and 508b is disposed to cover a portion of the top sheet member 502. The side sheets 508a, 508b can be provided with an embossed design, not shown. A pair of wings 509a, 509b project in the width direction WD on the sanitary napkin 501. Adhesive portions are equipped on the wings 509a, 509b. The sanitary napkin 501 is mounted to an undergarment by the wings 509a, 509b, for example, folding toward a side that is not in contact with the skin and becoming attached to the crotch portion of the undergarment. (This state is not shown.)

An outer edge portion 510 on the front portion 505 of the sanitary napkin 501 has a curved shape to project in the longitudinal direction and in the width direction. An outer edge portion 511 on the back portion 507 of the sanitary napkin 501 has a curved shape to project in the longitudinal direction and in the width direction. Note that in this embodiment the longitudinal direction LD is one example of a first direction in the present invention, and is equivalent to a machine direction (MD) when the sanitary napkin 501 is being manufactured. Also, the width direction WD is one example of a second direction in the present invention; it is equivalent to a cross direction that is perpendicular to the machine direction (MD).

The entire surface or a portion of the top sheet member 502 of the sanitary napkin 501 can be liquid-permeable. In addition, that member can be composed of one sheet member, or it can be composed by joining a plurality of sheet members. In this embodiment, the top sheet member 502 is equipped a liquid permeable area between the joints to the sanitary napkin 501 of the side sheets 508a, 508b in the width direction WD of the sanitary napkin 501.

A leak-prevention zone 512 is equipped on the top sheet member 502. The leak-prevention zone 512 has an embossed pattern made by an embossing process, for example; a large pressing force is applied in the thickness direction TD to reduce the thickness of the absorbent body member 503. There are no limitations to the patterns of the leak-prevention zone 512.

The sanitary napkin 501 configured as described above receives excreta such as menstrual blood, etc., at the top sheet member 502. The excreta permeates into the top sheet member 502 to be absorbed by the absorbent body member 503. The back sheet member 504 disposed at the non-skin contact side is not liquid-permeable so excreta is retained in an absorbed state in the absorbent body member 503, without permeating to the non-skin contact side.

1-2. Top Sheet Member

Figure 3:
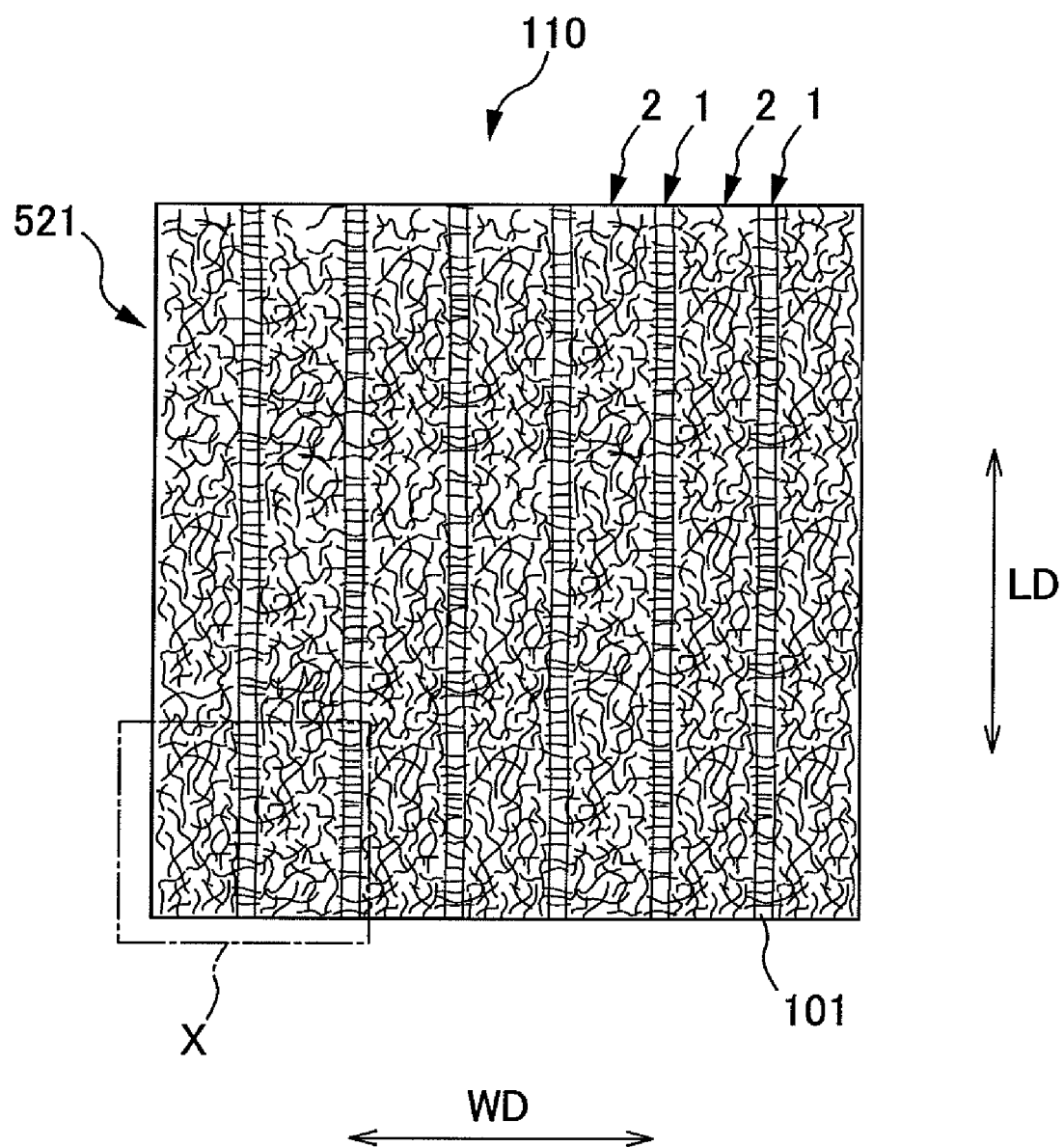
FIG. 3 is a plan view showing a first surface of nonwoven fabric used in a top sheet member.
Figure 4:
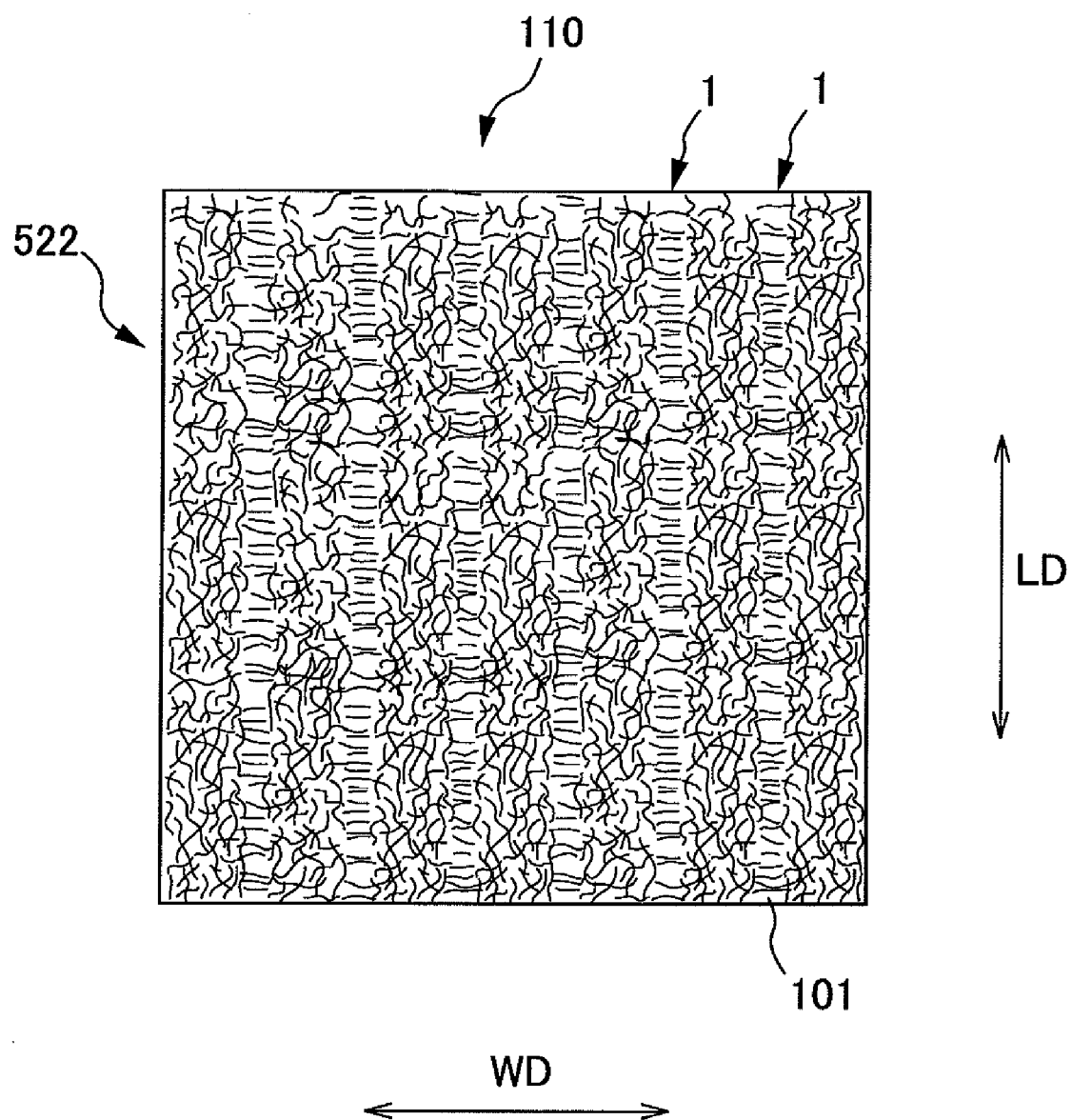
FIG. 4 is a plan view of a second surface opposite to the first surface as described in FIG. 3.
Figure 5:
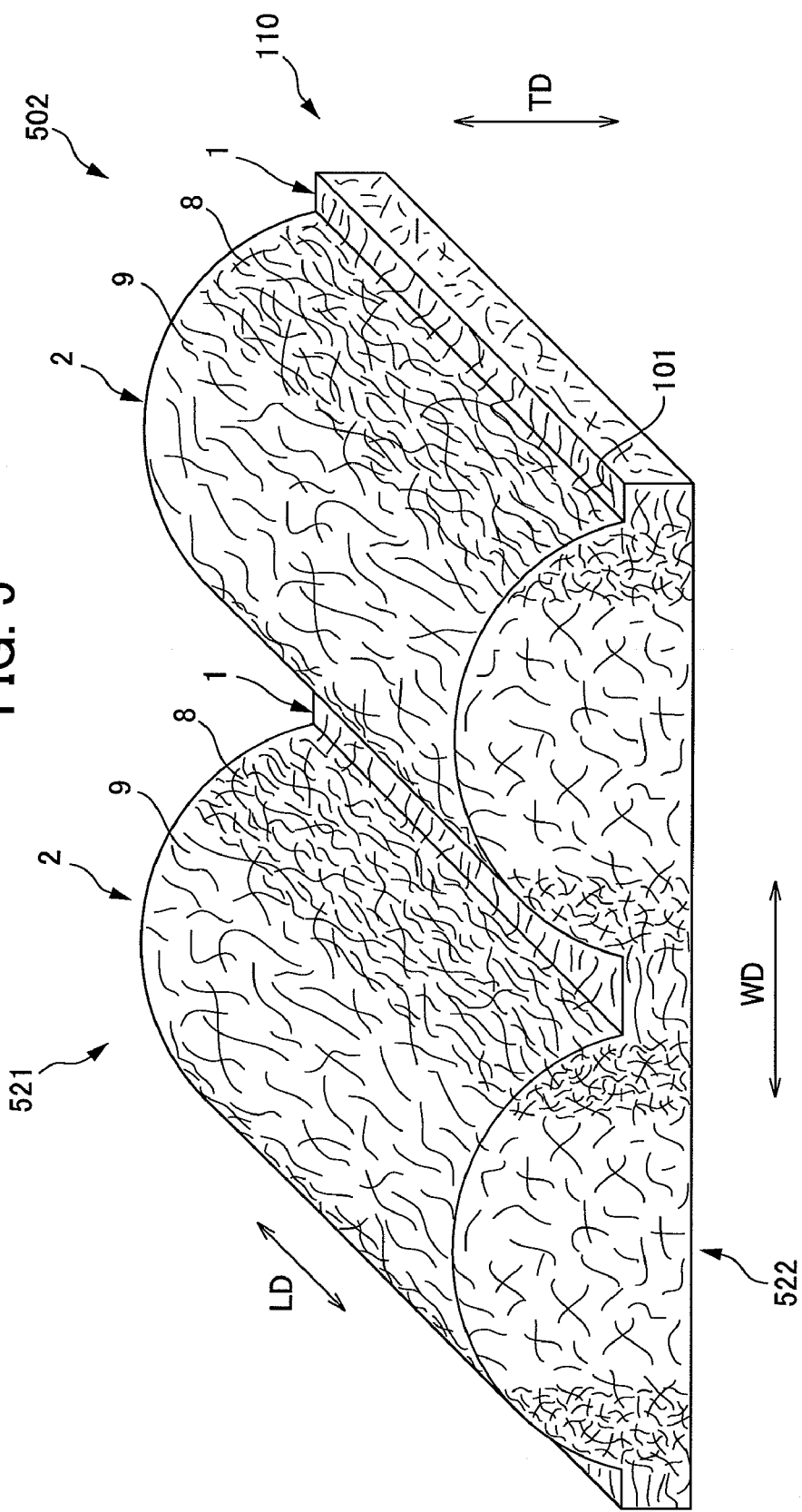
FIG. 5 shows an expanded perspective view of an area X as described in FIG. 3.

FIG. 3 is a plan view showing a first surface 521 of nonwoven fabric used in a top sheet member 502. FIG. 4 is a plan view of a second surface 522 opposite to the first surface 521 as described in FIG. 3. FIG. 5 is an expanded perspective view of a part showing a configuration of nonwoven fabric corresponding to the area demarcated with X in FIG. 3. Suitably, the following will now explain FIG. 5 with reference to FIGS. 1 and 2.

The top sheet member 502 is composed of the liquid-permeable nonwoven fabric 110 formed with gaps between fibers internally. In the first surface 521 that is the skin-contact surface side, the nonwoven fabric 110 that compose the top sheet member 502 have a plurality of raised ridge portions 2 formed to extend in the longitudinal direction LD, and a plurality of groove portions 1 adjacent to the plurality of raised ridge portions 2 in the width direction WD, formed to extend in the longitudinal direction LD. The raised ridge portions 2 are one example of raised ridge portions according to the present invention; the groove portions 1 are one example of concave portions according to the present invention. In the nonwoven fabric 110, the second surface 522 of the side that contacts the absorbent body member 503 is flat compared to the first surface 521.

Each of the plurality of raised ridge portions 2 has side edge portions 8, and central portion 9 that are thicker than the side edge portions 8 between both side edge portions 8. The fiber density in the thickness direction TD of the nonwoven fabric 110 at the side edge portions 8 is substantially uniform. At the same time, the side edge portions 8 have a higher fiber density than the overall average fiber density of the raised ridge portions 2 combining the side edge portions 8 and the central portion 9. The fiber density in the thickness direction TD of the nonwoven fabric 110 at the central portion 9 is substantially uniform. At the same time, the side edge areas 9 has a lower fiber density than the overall average fiber density of the raised ridge portions 2 combining the side edge portions 8 and the central portion 9.

According to the configuration described above, in the plurality of raised ridge portions 2, the fiber density in the thickness direction TD for each of the side edge portions 8 is substantially uniform, and at each of the central portion 9, the fiber density in the thickness direction TD is substantially uniform. Hence, the menstrual blood that passes through the plurality of raised ridge portions 2 is smoothly transferred to the absorbent body member 503 without building up at the second surface 522. Particularly, the central portion 9 has a low fiber density, so larger volumes of menstrual blood can pass through that portion compared to the side edge portions 8, and are smoothly guided to the absorbent body member 503. Also, although the fiber density is high at the side edge portions 8, the fibers have not been made into film, so the wearer does not have foreign-body sensation, or a poor feeling against the skin.

Furthermore, each of the side edge portions 8 of the plurality of raised ridge portions 2 has a higher fiber-density than the central portion 9, and the rigidity of the fibers is high. Hence, even if external pressure is applied to the raised ridge portions 2, the central portion 9 is supported by the highly rigid side edge portions 8 positioned at both sides of the central portion 9. This makes it difficult for external pressure and the like to cause the plurality of raised ridge portions 2 to collapse. In addition, this also makes it possible to prevent the raised ridge portions 2 from being crushed under the weight of large volumes of bodily fluids.

Since it is difficult to collapse the raised ridge portions 2 by external pressure and the like, the air permeability of the groove portions 1 is particularly favorable. That is, the top sheet member 502 is superior in air permeability in the longitudinal direction LD. On the other hand, in the width direction WD, which is shorter in length compared to the length direction LD, the spread of menstrual blood is suppressed by way of the raised ridge portions 2, which are continuous in the length direction LD, and by the fiber area that is on the bottom of the groove portions 1. Accordingly, the top sheet member 502 is configured to be superior in preventing menstrual blood in the absorbent article (sanitary napkin 501) from leaking, as well as maintaining air permeability.

1-2-1. Shape

The following will now explain in detail the shape of the nonwoven fabric 110 that is used in the top sheet member 502 with suitable reference to FIGS. 1 to 5. The nonwoven fabric 110 is formed with a plurality of groove portions 1 and a plurality of raised ridge portions 2 in the fiber assembly in which fibers have a degree of freedom. One side of the fiber assembly is supported by a supporting member having a portion that allows a fluid, described below, to pass through. The plurality of groove portions 1 and the plurality of raised ridge portions 2 are formed by a portion of the fibers of the fiber assembly being moved by the fluid, composed mainly of a gas, being blown through the fiber assembly.

The plurality of groove portions 1 is formed in parallel in the nonwoven fabric 110 at substantially equal distances along the longitudinal direction LD on the first surface 521 side of the nonwoven fibers 110. In this embodiment, the plurality of groove portions 1 is formed in parallel at equidistance spacing, but this is not meant to be a limitation. The spacing between adjacent groove portions 1 can be different. It is also acceptable that the spacing of the groove portions 1 is not parallel, but can be varied.

Furthermore, raised ridge portions 2 are formed Furthermore, raised ridge portions 2 are formed between two adjacent groove portions 1 and 1. A plurality of raised ridge portions 2 and 2 are formed in parallel at equidistant spacing, in the same way as the groove portions 1. The heights (the thickness direction TD) of the raised ridge portions 2 of the nonwoven fabric 110 of this embodiment are substantially uniform, but it is acceptable that the heights of mutually adjacent raised ridge portions 2 to be different.

The heights of the raised ridge portions 2 that are the distances in the thickness direction in the nonwoven fabric 110 of this embodiment are between 0.3 and 15 mm; preferably between 0.5 and 5 mm. The lengths in a second direction (hereinafter referred to as the lateral direction or the cross direction) that is perpendicular to a first direction per raised ridge portion 2 is between 0.5 to 30 mm; preferably 1.0 to 10 mm. Also, the distance between peaks of adjacent raised ridge portions 2 and 2 is 0.5 to 30 mm; preferably between 3 to 10 mm.

Also, the heights (the distance in the thickness direction TD) of the nonwoven fabric 110 of an area formed of groove portions 1 are between 0 to 90% with regard to the heights of raised ridge portions 2, preferably between 1 to 50%; more preferably between 5 to 20%. The width of the groove portions 1 is between 0.1 to 30 mm; preferably from 0.5 to 10 mm. Also, the distances (pitches) between adjacent groove portions 1 sandwiching the raised ridge portions 2 are between 0.5 to 20 mm; preferably from 3 to 10 mm.

By configuring the groove portions 1 and raised ridge portions 2 as described above, it is difficult for a mass of a predetermined liquid to spread widely across the surface, if the nonwoven fabric 110 of this embodiment is used as the surface sheet (top sheet) of an absorbent article, for example. Also, even if the raised ridge portions 2 are crushed under excessive external pressure, the spaces formed by the groove portions 1 are easily maintained. Therefore, even if a predetermined liquid is excreted while external pressure is being applied, it is difficult for the liquid to spread widely across the surface. Furthermore, even in cases where the predetermined liquid, which has been absorbed into a part of the absorbent article and is now under external pressure and tries to flow back, the nonwoven fabric 110 surface is formed to be uneven so there is less surface area for contact between the nonwoven fabric 110 and the skin, making it difficult for the liquid to widely adhere to the skin.

The following will now explain how to measure the heights, pitches and widths of the groove portions 1 and raised ridge portions 2. For example, place the nonwoven fabric 110 on a table without any pressure applied to the nonwoven fabric 110, then use a microscope to take a sectional photograph or sectional image of the nonwoven fabric 110 and measure dimensions. Note that the sample nonwoven fabric 110 should be cut passing through the raised ridge portions 2 and the groove portions 1.

When measuring height (the distance in the thickness direction TD), measure from the lowest position (in other words, the table top) of the nonwoven fabric 110 to the highest positions of the raised ridge portions 2 and the groove portions 1 toward the upward direction.

Also, to measure pitches, measure the distance between peaks of adjacent raised ridge portions 2. Measure the groove portions 1 in the same way.

To measure widths, measure the maximum width of the bottom face of the raised ridge portions 2 from the lowest position (in other words, the table top) of the nonwoven fabric 110 toward the upward direction. Measure the maximum width of the bottom face of the groove portions 1 in the same way.

There is no particular limitation to the shapes of the raised ridge portions 2. For example, dome shapes, trapezoidal shapes, triangular shapes, Ω-shapes, and square shapes are all possible. To enhance the feel of the nonwoven fabric 110 against the skin, it is preferred that the area near the peak of the raised ridge portions 2 and the sides be curved surfaces.

Also, to maintain the spaces of the groove portions 1 when the raised ridge portions 2 are crushed by external pressure, it is preferred that the widths of the raised ridge portions 2 be narrower from the bottom face to the peak surface. A preferred shape of the raised ridge portion 2 is a curved line (curved surface) such as a substantial dome shape.

1-2-2. Fiber Orientation

The following will now explain in detail the orientation of fibers in the nonwoven fabric 110 that is used in the top sheet member 502 with suitable reference to FIGS. 1 to 5. In the nonwoven fabric 110, areas are formed with a different percent content of fabric orientated in a predetermined direction relating to the fibers 101 that compose the nonwoven fabric 110. Examples of each of the different areas include the side edge portions 8 and the center portion 9 that compose groove portions 1 and the raised ridge portions 2 (see FIG. 3).

In relation to the fibers that compose the nonwoven fabric 110, the nonwoven fabric 110 includes first orientation fibers oriented along the longitudinal direction LD, and second orientation fibers oriented along the width direction WD. In the plurality of raised ridge portions 2, the side edge portions 8 have more first orientation fibers compared to the central portion 9. In addition, the fibers that compose the bottom portion of each of the plurality of the groove portions 1 have more second orientation fibers compared to the fibers that compose the central portion 9 of each of the plurality of raised ridge portions 2. Furthermore, there are more obliquely orientated fibers in the thickness direction TD in the central portion 9 of each of the plurality of the raised ridge portions 2 compared to the side edge portions 8 of each of the plurality of raised ridge portions 2.

In the first orientation fibers, the state of the fibers being orientated along the longitudinal direction LD refers to a state where the nonwoven fabric or the fiber webs being conveyed out via the machine that manufactures the nonwoven fabric is orientated within a range of +45° to −45° with respect to the machine direction (MD). Also, the fibers (fibers having an orientation near to the longitudinal direction LD) orientated along the longitudinal direction LD are called longitudinally-orientated fibers. Therefore, the longitudinally-orientated fibers are defined as the first orientation fibers.

In the second orientation fibers, the state of the fibers being orientated along the width direction WD refers to a state where the fibers 101 are orientated within a range of +45° to −45° with respect to the direction that is perpendicular (CD) to the machine direction (MD), the width direction WD. In addition, the fibers (fibers having an orientation near to the width direction WD) orientated along the width direction WD are called laterally-orientated fibers. Therefore, the laterally-orientated fibers are defined as the second orientation fibers.

Fibers having an oblique orientation to the thickness direction TD are fibers 101 in an oblique state orientated in the thickness direction TD within a range of +75° to −75°, preferably +45° to −45° with regard to the horizontal plane.

In each of the plurality of raised ridge portions 2 in the nonwoven fabric 110 that is used in the top sheet member 502, there are more fibers in the side edge portions 8 that are orientated in the longitudinal direction LD compared to the central portion 9. In other words, the fibers 101 at the side edge portions 8 are formed so that the percent content of the longitudinally-orientated fibers is higher than the percent content of the longitudinally-orientated fibers at the central portion 9 (the area sandwiched by the sides 8 on the raised ridge portions 2).

For example, the percent content of the longitudinally-orientated fibers at the side edge portions 8 is between 55 to 100%; more preferably between 60 to 100%. If the percent content of the longitudinally-orientated fibers at side edge portions 8 is less than 55%, the side edge portions 8 may experience unnecessary stretching caused by line tension during the manufacturing process. In addition, if the stretching of the side edge portions 8 is excessive, the groove portions 1 and the central portion 9, described below, may also be stretched by line tension, which may lead to destruction of the shape. In other words, because line tension occurs in the manufacturing process, mainly in the side edge portions 8 of the raised ridge portions 2, the increased percent content of the longitudinally-orientated fibers in the side edge portions 8 prevents the side edge portions 8 from experiencing unnecessary stretching. By drawing out to a proper degree, it becomes more difficult to crush the bulk of the raised ridge portions 2.

The fibers that compose the bottom portion of each of the plurality of the groove portions 1 in the nonwoven fibers 110 used in the top sheet member 502 have more second orientation fibers compared to the fibers that compose the central areas 9 of each of the plurality of the raised ridge portions 2; in other words, there are more fibers orientated in the lateral, or width direction WD. The groove portions 1, as described above, are areas upon which the fluid (for example, hot air) composed mainly of gas is directly blown. Therefore, the longitudinally-orientated fibers at the groove portions 1 are displaced to the side edge portions 8. The laterally-orientated fibers remain at the groove portions 1. Hence, the percent content of the laterally-orientated fibers is higher at the groove portions 1 than that of the longitudinally-orientated fibers.

For example, the content percentage of fibers oriented toward the longitudinal direction at the groove portions 1 is a minimum of 10% less than the content percentage of the laterally-oriented fibers at the central portions 9. Therefore, the content percentage of the longitudinally-oriented fibers is the least and the content percentage of the laterally-oriented fibers is the greatest at the groove portions 1 at the nonwoven fabric 110. Specifically, the content percentage of the laterally-oriented fibers is between 55 to 100%; preferably between 60 to 100%. When the content percentage of the laterally-oriented fibers is less than 55%, the basis weight of the groove portions 1, as described below, is low, so it is more difficult to increase the strength of the nonwoven fabric in the width direction. When doing so, if the nonwoven fabric 110 is used as the top sheet (surface sheet) of an absorbent article, for example, friction with a body during use of the absorbent article causes it to be misdirected to the width direction, and there is the danger that it can be damaged.

There are more fibers orientated obliquely in the thickness direction TD in the central portion 9 of each of the plurality of the raised ridge portions 2 compared to the side edge portions 8 of each of the plurality of raised ridge portions 2. The central portions 9 are areas sandwiched by the side edge portions 8 on both sides of the raised ridge portions 2. These are areas where the percent content of the longitudinally-orientated fibers is lower than the side edge portions 8. It is preferred that the longitudinally-orientated fibers and the laterally-orientated fibers be moderately mixed at the central portions 9.

For example, the percent content of the longitudinally-orientated fibers of the central portions 9 is a minimum of 10% lower than the percent content of the longitudinally-orientated fibers of the side edge portions 8, and is a minimum of 10% higher the percent content of the laterally-orientated fibers in the bottom portion of the groove portions 1, described below. Specifically, it is preferred that the content percentage of the longitudinally-orientated fibers at the central portions 9 is in a range between 40 to 80%. More preferably, the longitudinally-orientated fibers and the laterally-orientated fibers in the central portion 9 are in a range of +75° to −75° in the thickness direction TD with regard to the horizontal plane, and even more preferably, fibers having an oblique orientation are within a range of +45° to −45°. This places a load on the central portion 9 thereby reducing the thickness of the raised ridge portions 2, but if the load is removed, the raised ridge portions 2 will easily return to their original thickness due to the stiffness of the fibers 2 orientated in the thickness direction TD. In other words, these are nonwoven fabric that have high compression recoverability. In addition, because it is easy for the fluid to move along the orientated fiber, permeation of the fluid in the raised ridge portions 2 is facilitated due to each of the fibers obliquely orientated in the thickness direction TD.

Following is an outline of the method used to measure fiber orientation with a digital microscope VHX-100 made by Keyence Corporation. (1) Set a sample so that the length direction is in the proper direction on the observation stage. (2) Focus the lens on the fibers at the front of the sample, excluding the fibers that irregularly protrude to the front. (3) Set photographic depth (to the back) and create a 3D image on a PC monitor. Next, (4) convert the 3D image into a 2D image. (5) Draw a plurality of equally spaced, parallel lines on the monitor at any suitable time in the length direction in the range to measure. (6) In each fragmented cell drawn with parallel lines and observe whether the fiber orientation is in the first direction (length direction) or in the second direction (width direction) then measure the number fibers facing each direction. Then, (7) calculate the ratio of the number of fibers in the fiber orientation facing the first direction (the length direction) and the ratio of the number of fibers in the fiber orientation in the second direction (width direction) for the entire number of fibers in the set range to measure and calculate.

1-2-3. Fiber Compression

As shown in FIG. 3 to 5, the fiber density is adjusted to be less at the groove portions 1 compared to the raised ridge portions 2. Also, the fiber density of the groove portions 1 can be freely adjusted by several conditions, such as the amount of blown fluid (for example hot air) composed of mainly gas, and the tension. Also, the raised ridge portions 2 are formed to have a greater fiber density than the fiber density of the groove portions 1.

The fiber density at the bottom of the groove portions 1, specifically is a maximum of 0.18 $g/cm^3$; preferably between 0.002 to 0.18 $g/cm^3$; more preferably between 0.005 to 0.05 $g/cm^3$. When the fiber density of the bottom portion of the groove portions 1 is less than 0.002 $g/cm^3$, and the nonwoven fabric 110 is used in an absorbent article, for example, the nonwoven fabric 110 can be easily damaged. If the fiber density at the bottom portion of the groove portions 1 is greater than 0.18 $g/cm^3$, it is difficult for the liquid to travel downward and will be retained at the groove portions 1, giving the user a moist sensation.

Fiber density is adjusted to be greater at the raised ridge portions 2 compared to the groove portions 1. Furthermore, the fiber density of the raised ridge portions 2 can be freely adjusted by several conditions, such as the amount of blown fluid (for example hot air) composed of mainly gas, and the tension.

Fiber density at the central portions 9 of the raised ridge portions 2 is between 0 to 0.20 $g/cm^3$; preferably between 0.005 to 0.20 $g/cm^3$; more preferably between 0.007 to 0.07 $g/cm^3$ for example. If the fiber density of the central portions 9 is less than 0.005 $g/cm^3$, not only is it easier for the central portions 9 to be crushed by the weight of the liquid contained in the central portions 9 or by external pressure, but it also becomes easier for the liquid once absorbed in the absorbent article to reverse back, under the applied pressure. If fiber density at the central portions 9 is greater than 0.20 g/cm$^3$, it is difficult for the liquid contained at the central portions 9 to travel downward and will be retained in the groove portions 9, giving the user a moist sensation.

Furthermore, fiber density at the sides 8 of the raised ridge portions 2 can be freely adjusted by several conditions, such as the amount of blown fluid (for example hot air) composed of mainly gas, and the tension. Specifically, the fiber density of the sides 8 is between 0 to 0.40 g/cm$^3$; preferably between 0.007 to 0.25 g/cm$^3$; more preferably 0.01 to 0.20 g/cm$^3$ for example. If fiber density at the sides 8 is less than 0.007 g/cm$^3$, there are cases that the sides 8 will become stretched by line tension. If fiber density at the central portions 8 is greater than 0.40 g/cm$^3$, it is difficult for the liquid contained at the sides 8 to travel downward. Thus, the liquid will be retained at the sides 8, giving the user a moist sensation.

1-2-4. Basis Weight

The average basis weight of the overall fiber of the nonwoven fabric 110 is between 10 to 200 g/m$^2$; preferably 20 to 100 g/m$^2$. For example, if the nonwoven fabric 110 is used in the top sheet (surface sheet) of an absorbent article, and the average basis weight is less than 10 g/m$^2$, the surface sheet can be easily damaged while in use. Also, if the average basis weight of the nonwoven fabric 110 is greater than 200 g/m$^2$, it is difficult for liquid to move downward.

As shown in FIG. 3 to 5, the basis weight of the fibers 101 at the groove portions 1 is adjusted to be less compared to the raised ridge portions 2. Also, the basis weight of the bottom portion of the groove portions 1 is adjusted so that it is less compared to the average basis weight of entire nonwoven fabric including the bottom portion of the groove portions 1 and the raised ridge portions 2. Specifically, the basis weight of the bottom of the groove portions 1 is between 3 to 150 g/m$^2$; preferably between 5 to 80 g/m$^2$. If the basis weight of the bottom portion of the groove portions 1 is less than 3 g/m$^2$, and the nonwoven fabric 110 is used as the top sheet (surface sheet) of an absorbent article, for example, the surface sheet can be easily torn during use. If the basis weight of the bottom of the groove portions 1 is greater than 150 g/m$^2$, it is difficult for the liquid contained at the groove portions 1 to travel downward and will be retained in the groove portions 1, giving the user a moist sensation.

The average basis weight of the fiber 101 at the raised ridge portions is adjusted to be greater compared to the groove portions 1. The basis weight of the central portions 9 at the raised ridge portions 2 is between 15 to 250 g/m$^2$; preferably between 20 to 120 g/m$^2$. If the basis weight of the central portions 9 is less than 15 g/m$^2$, not only is it easier for the central portions 9 to be crushed by the weight of the liquid contained at the central portions 9 or by external pressure, but it also becomes easier for the liquid absorbed in the absorbent article to reverse back, under the applied pressure. If the basis weight of the central portions 9 is greater than 250 g/m$^2$, it is difficult for the liquid to travel downward and will be retained at the central portions 9, giving the user a moist sensation.

Furthermore, the basis weight at the sides 8 of the raised ridge portions 2 can be freely adjusted by several conditions, such as the amount of blown fluid (for example hot air) composed of mainly gas, and the tension. Specifically, the basis weight at the sides 8 is between 20 to 280 g/m$^2$; preferably between 25 to 150 g/m$^2$. If the basis weight at the sides 8 is less than 20 g/m$^2$, there is the possibility of the sides 8 experiencing stretching caused by line tension. If the basis weight at the sides 8 is greater than 280 g/m$^2$, it is difficult for the liquid contained at the sides 8 to travel downward and will be retained in the sides 8, giving the user a moist sensation.

Also, the basis weight at the bottom of the groove portions 1 is adjusted so that it is less compared to the average basis weight of entire nonwoven fabric of the raised ridge portions 2 composed of the sides 8 and the central portions 9. For example, the basis weight at the bottom of the groove portions 1 is a maximum of 90% of the average basis weight of the raised ridge portions 2; between 3 to 90%; more preferably between 3 to 70%. If the basis weight at the bottom of the groove portions 1 is greater than 90% of the average basis weight of the raised ridge portions 2, there will be greater resistance to the liquid which has seeped into the groove portions 1 to move downward of the nonwoven fabric 110, which can cause the liquid to leak from the groove portions 1. If the basis weight at the bottom portion of the groove portions 1 is less than 3% with regard to the average basis weight of the raised ridge portions 2, and the nonwoven fabric is used as the top sheet (surface sheet) of an absorbent article, for example, the surface sheet can be easily damaged during use of the absorbent article.

1-2-5. Others

According to the embodiment described above, the use of a top sheet with a structure of the nonwoven fabric 110 in an absorbent article makes it easier for fluid to pass through the groove portions 1 and for the raised ridge portions 2 to retain the fluid because of the porous structure.

The fiber density of the fibers 101 of the bottom portion of the groove portions 1 is lower compared to the other areas and the basis weight is low, so it is appropriate for the penetration of liquid. Furthermore, the fibers 101 at the bottom portion of the groove portions 1 are orientated in the width direction WD so it is possible to prevent the liquid from flowing too far in the longitudinal direction of the nonwoven fabric 110 in the groove portions 1 and spreading widely. The fibers 101 are orientated in the width direction WD (CD orientation) of the groove portions 1, so regardless of the fact that the basis weight is lower compared to other areas, the strength of the nonwoven fabric 110 in the width direction WD (CD strength) is increased.

The raised ridge portions 2 are adjusted so their basis weights are higher compared to other areas, but because this increases the number of fibers, the number of fusion points also increases and the porous structure is maintained.

1-2-6. Manufacturing Method

Figure 6:
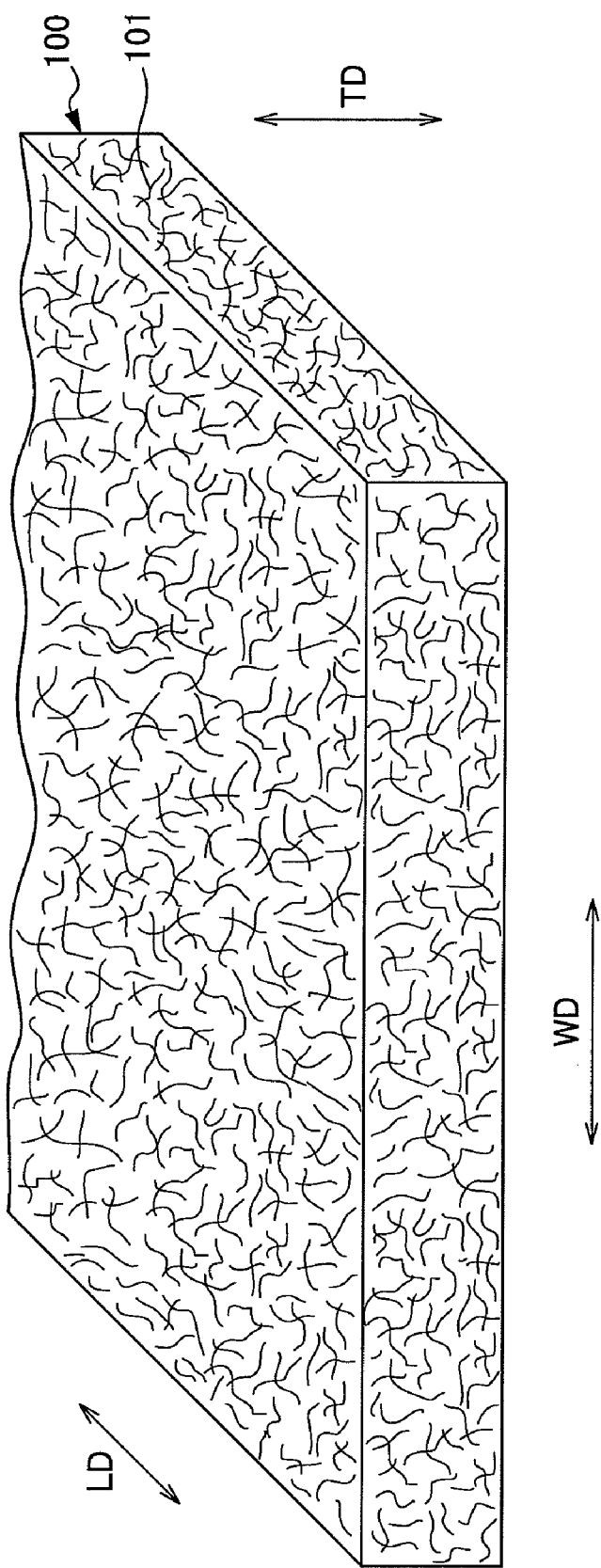
FIG. 6 shows a perspective view of a fiber web.
Figure 7:
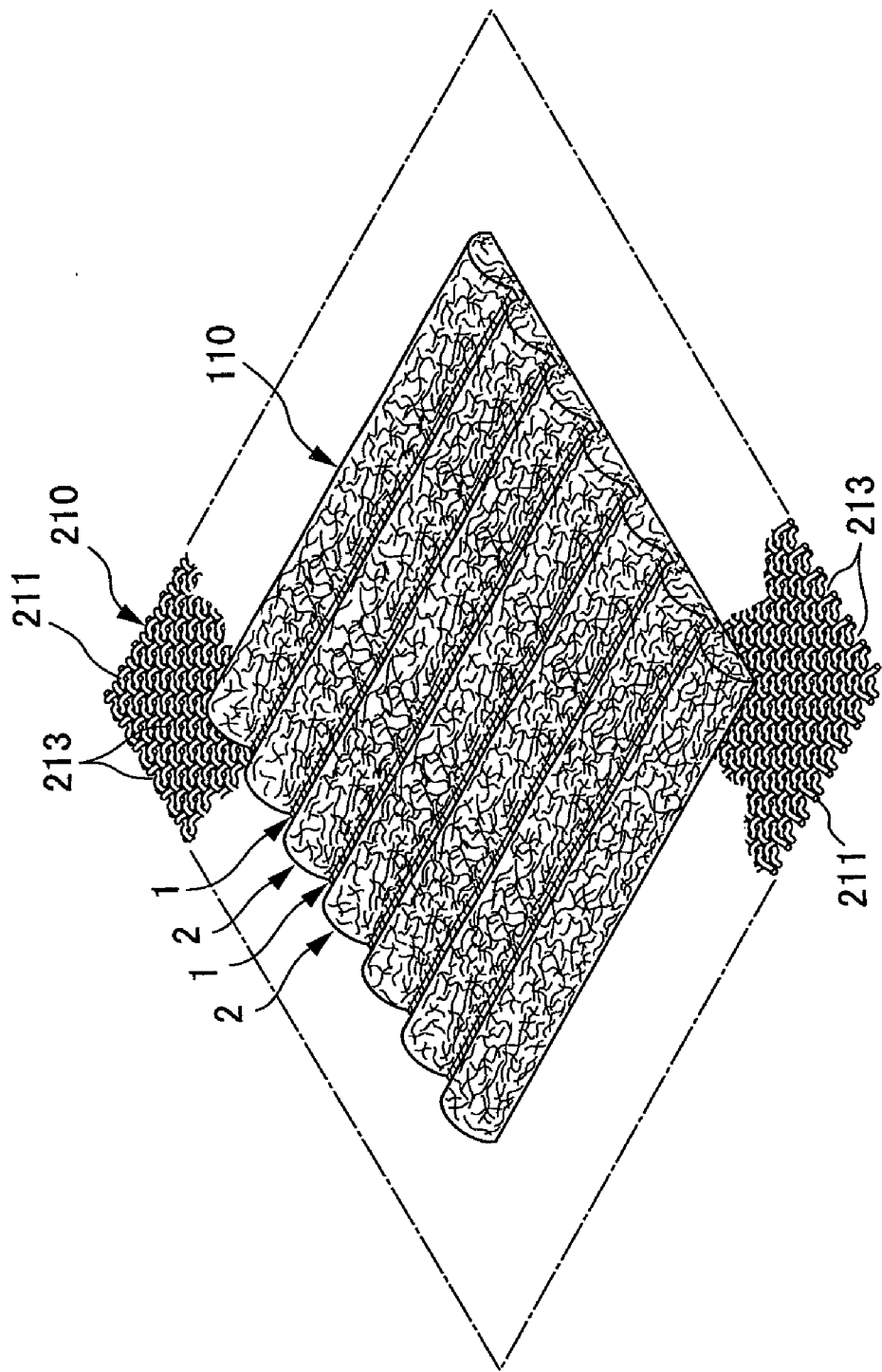
FIG. 7 shows nonwoven fabric as described in FIGS. 3 to 5, supported by a mesh supporting member, being manufactured.
Figure 8:
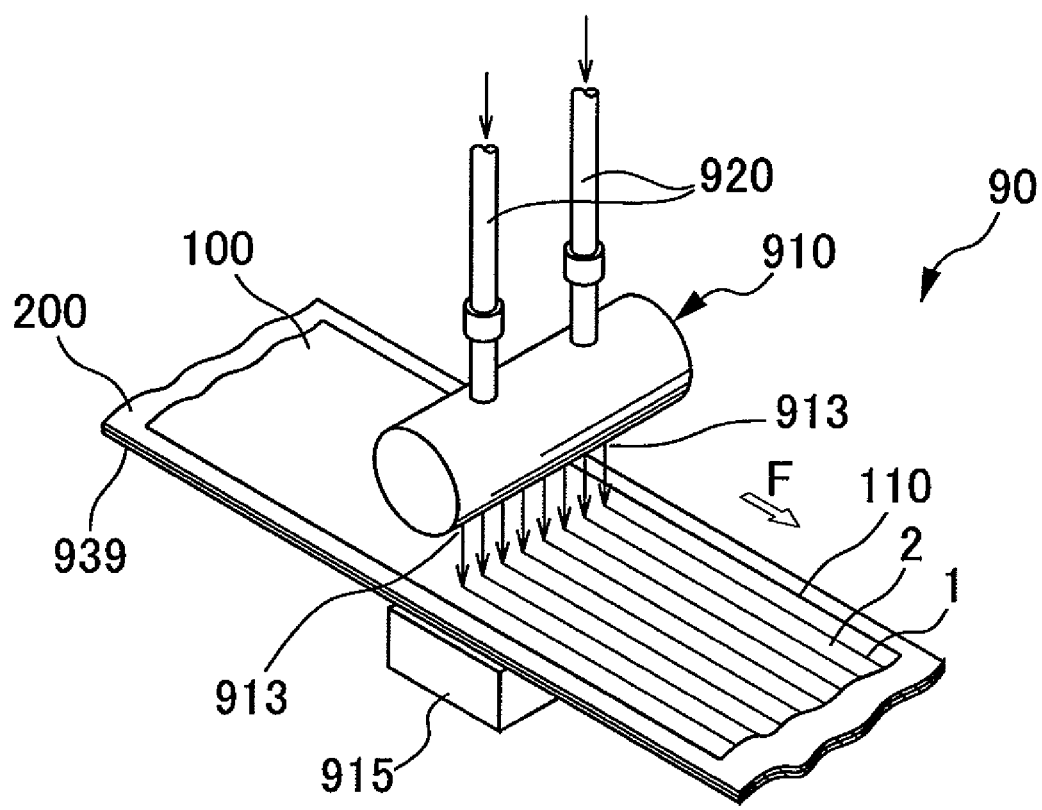
FIG. 8 is a perspective view to explain the nonwoven fabric manufacturing apparatus.

FIG. 6 is a perspective view of a fiber web. FIG. 7 shows the fiber web as described in FIG. 6 blown from above by a gas, the fiber web supported by a mesh supporting member, to show the nonwoven fabric as shown in FIGS. 3 to 5 being manufactured. FIG. 8 is a perspective view to explain the nonwoven fabric manufacturing apparatus The following will now explain the method for manufacturing the nonwoven fabric 110 used in the top sheet member 502 of an absorbent article of the present invention, with reference to FIGS. 6 to 8.

First, the fiber web 100 is placed on a top surface of the mesh supporting member 210 which is an air-permeable support member. Said another way, the fiber web 100 is supported from a bottom side by the mesh supporting member 210 (see FIG. 7). As shown in FIG. 8, it is possible to manufacture the nonwoven fabric 110 of this embodiment by moving the mesh supporting member 210 or air-permeable support member 200 in a predetermined direction (F) while supporting the fiber web 100 and continuously blowing a gas from a top side of the fiber web 100 as it is being moved.

As shown in FIG. 7, the mesh supporting member 210 as the air-permeable support member 200 is formed by weaving a plurality of wires 211 of a predetermined thickness, which are non-air-permeable portions. By weaving the plurality of wires 211 to leave a predetermined space open, the mesh supporting member formed with a plurality of air-permeable holes 213 is obtained.

The mesh supporting member 210 in FIG. 7 is formed with a plurality of holes 213 that have small diameters. The gas blows from the top side of the fiber web 100 and passes downward unhindered by the mesh supporting member 210. This mesh supporting member 210 prevents the fibers 101 from moving to a downward direction of the mesh supporting member 210 but does not greatly vary the flow of the fluid composed mainly of a gas being blown.

For that reason, the fibers 101 that compose the fiber web 100 are moved in a predetermined direction by the gas blow mainly from the top side. Specifically, downward movement is limited by the mesh supporting member 210 so the fibers 101 are moved in a direction along the surface of the mesh supporting member 210.

For example, the fibers 101 in the area blown by the gas are moved from that area to an area not blown by the gas in the surrounding area. Then, the area blown by the gas moves in a predetermined direction, so an area is formed on the fibers 101 where gas is continuously blown in a predetermined direction. The result is that the fibers 101 move to side directions in the consecutive areas.

This causes the groove portions 1 to be formed and the fibers 101 of the groove portions 1 to be moved and oriented in the width direction WD. Also, the raised ridge portions 2 are formed between the two adjacent groove portions 1 and 1, the fiber density of the sides in the raised ridge portions 2 increases and the fibers 101 become oriented in the longitudinal direction LD.

As shown in FIG. 8, the nonwoven fabric manufacturing apparatus 90 that manufactures the nonwoven fabric 110 of this embodiment is provided with the air-permeable support member 200, and blowing means composed of a blowing unit 910 and an air pipe, not shown. The air-permeable support member 200 is configured to support the fiber web 100, which is the fiber aggregate, from one side. The blowing unit 910 is configured to blow a fluid composed mainly of a gas from the other side of the fiber web 100. The air pipe is configured to feed the fluid, composed mainly of a gas, to the blowing unit 910.

Here, in the nonwoven fabric manufacturing apparatus 90, the nonwoven fabric 110 is formed while the fiber web 100 is being sequentially moved by moving means. The moving means moves the fiber web 100 in a predetermined direction while the fiber web 100 is supported at one side by the air-permeable support member 200. Specifically, the fiber web 100 is moved in a predetermined direction F while being blown by a fluid mainly composed of a gas. As moving means, an example is a conveyor.

The air-permeable support member 200 can be suitably replaced depending on the nonwoven fabric to be manufactured. For example, to manufacture the nonwoven fabric 110 of this embodiment, it is possible to use the mesh supporting member 210 described above as the air-permeable support member 200. The following will now explain using the mesh supporting member 210 described above as the air-permeable support member 200.

As described above, the conveyor, not shown, moves the mesh supporting member 210 to predetermined direction F while it is supporting the fiber web 100 from the bottom side thereof (see FIG. 8). Specifically, the fiber web 100 is moved to pass the bottom side of the blowing unit 910. In addition, the fiber web 100 is moved to pass the inside of a heater unit (not shown) which is a heating means, and is opened at both sides.

The blowing means is provided a pneumatic unit, not shown, and the blowing unit 910. The pneumatic unit, not shown, is linked to the blowing unit 910 via the air pipes 920. The air pipes 920 are connected to enable the passing of air to an upper side of the blowing unit 910. The blowing unit 910 is formed with a plurality of jet holes 913 at predetermined spaces.

The gas that is fed from the pneumatic unit, not shown, to the blowing unit 910 via the air pipes 920 is linked blown out from the plurality of jet holes 913. The gas blown out from the plurality of jet holes 913 is blown continuously onto the top surface of the fiber web 100. Specifically, the gas blown out from the plurality of jet holes 913 is blown continuously onto the top surface of the fiber web 100 being moved in the predetermined direction F by the conveyor.

A suction unit 915 arranged at a bottom side of the mesh supporting member 210, below the blowing unit 910, takes in the gas blown from the blowing unit 910 and passed through the mesh supporting member 210. By taking in the gas by the suction unit 915, it is possible to position the fiber web 100 to stick to the mesh supporting member 210.

The suction by the suction unit 915 can be of a strength to the degree that the fibers 101 of the areas being blown by the fluid, composed mainly of a gas, are pushed to the mesh supporting member 210. It is possible to prevent the shape of the fiber web 100 from becoming disarrayed by the fluid, composed of mainly a gas, striking the non-air-permeable portions (the wire 211 of the mesh supporting member 210) of the air-permeable support member 200 and rebounding, by suctioning the fluid, composed of mainly a gas, by the suction unit 915. It is possible to convey to inside the heater unit, not shown, while maintaining the shape of the grooves (concave/convex portion) formed by air current. It is preferred that the suction by the suction unit 915 be performed until the fiber web 100 is conveyed into the heater unit.

Also, by drawing in the fluid, composed mainly of a gas, from the bottom side of the mesh supporting member 210, the fibers of the area being blown by the fluid composed, mainly of a gas, are moved by being pushed to the mesh supporting member 210 side, so the fibers collect at the mesh supporting member 210 side. Also, at the raised ridge portions 2, by the fluid, composed mainly of a gas, which is being blown striking and rebounding from the non-air-permeable portion (the wires 211 of the mesh supporting member 210) of the air-permeable support member 200, the fibers 101 partially align toward the thickness direction.

The temperature of the fluid, composed mainly of a gas, blown from each of the jet holes 913 can be at room temperature, but to enable good formability of the groove portions (concave/convex), for example, it is possible to adjust the temperature to above the softening point of at least the thermoplastic fibers that compose the collection of fibers, and preferably above the softening point, to a temperature between +50° C. and −50° C. of the melting point. Because the fiber itself loses repulsive force when the fibers are softened, they can easily maintain their rearranged shapes by an air current. If the temperature is raised even further, the fibers will begin to melt together, making them maintain the shape of the groove portions (concave/convex) even more. This makes it possible to convey the fiber web to inside the heater unit while maintaining the shape of the grooves (concave/convex).

Note that the airflow rate and temperature of the fluid, composed mainly of a gas being blown, and the amount of suction, the permeability of the mesh supporting member 210, and the adjustment of the basis weight of the fiber web 100 can vary the shapes of the raised ridge portions 2. For example, if the amounts of the fluid, composed mainly of a gas, being blown and being taken in (drawn in) are substantially equal, or if there is a greater amount of fluid, composed mainly of a gas, being taken in (drawn in), the backside of the raised ridge portions 2 of the nonwoven fabric 115 (nonwoven fabric 110) is formed according to the shape of the mesh supporting member 210. Therefore, if the mesh supporting member 210 is flat, the backside of the nonwoven fabric 115 (nonwoven fabric 110) would also be flat.

Also, it is possible to convey to the heater unit, not shown, while maintaining the shapes of the groove portions (concave/convex) formed by the air current, either by conveying to the inside of the heater immediately after forming the groove portions (concave/convex) formed by the air current or at the same time, or cooling immediately forming the groove portions (concave/convex) with hot air (an air current of a predetermined temperature) then conveying to the heater unit.

The heater unit which is the heating means, has both ends open in the predetermined direction F. The fiber web 100 (nonwoven fabric 110) set on the mesh supporting member 210 is continuously moved with a predetermined time retained in the heated space formed inside the heater. For example, if the fibers 101 composing the fiber web 100 (nonwoven fabric 110) include thermoplastic fibers, it is possible to obtain nonwoven fabric 115 (nonwoven fabric 110) where fibers 101 are joined together by heat in the heater unit.

2. Second Embodiment 2-1. General Description

The general shape is a sanitary napkin that is the same as the first embodiment. Therefore, an explanation thereof will be omitted. (See section 1-1. General Description)

2-2. Top Sheet Member

Figure 9:
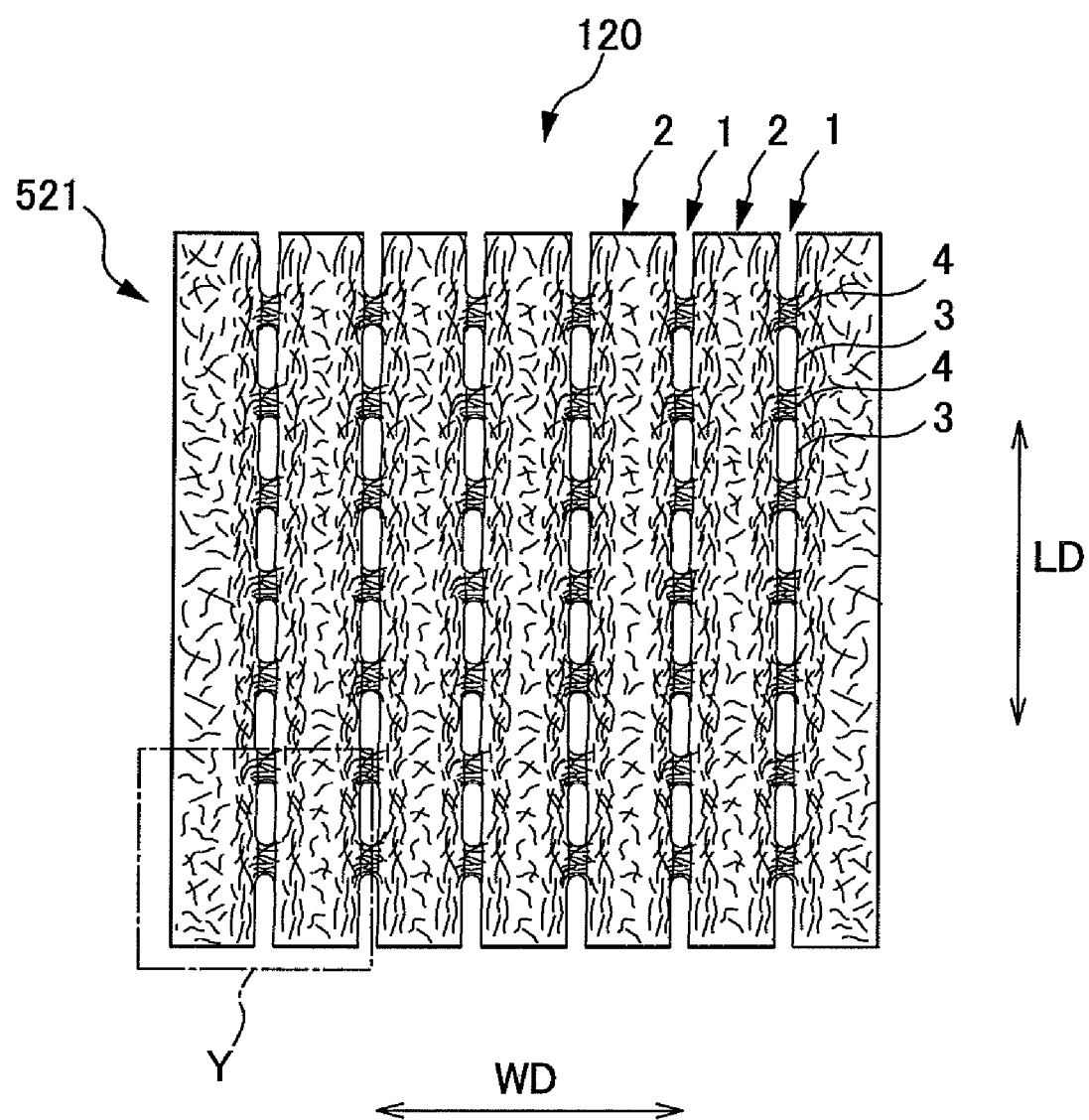
FIG. 9 is a plan view showing a first surface of nonwoven fabric according to a second embodiment, as used in a top sheet member of the sanitary napkin as described in FIG. 1.
Figure 10:
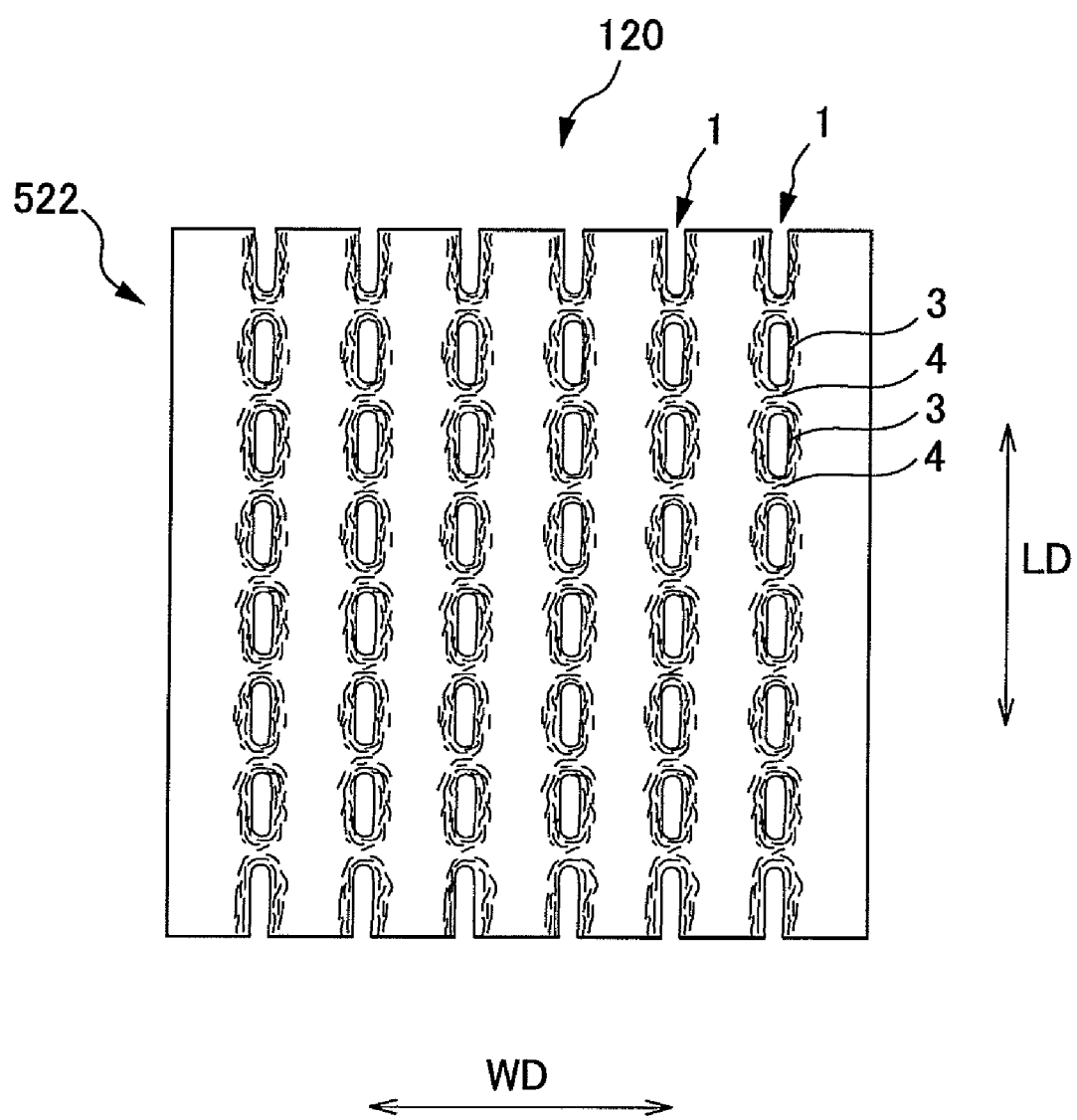
FIG. 10 is a plan view of a second surface opposite to the first surface as described in FIG. 9.
Figure 11:
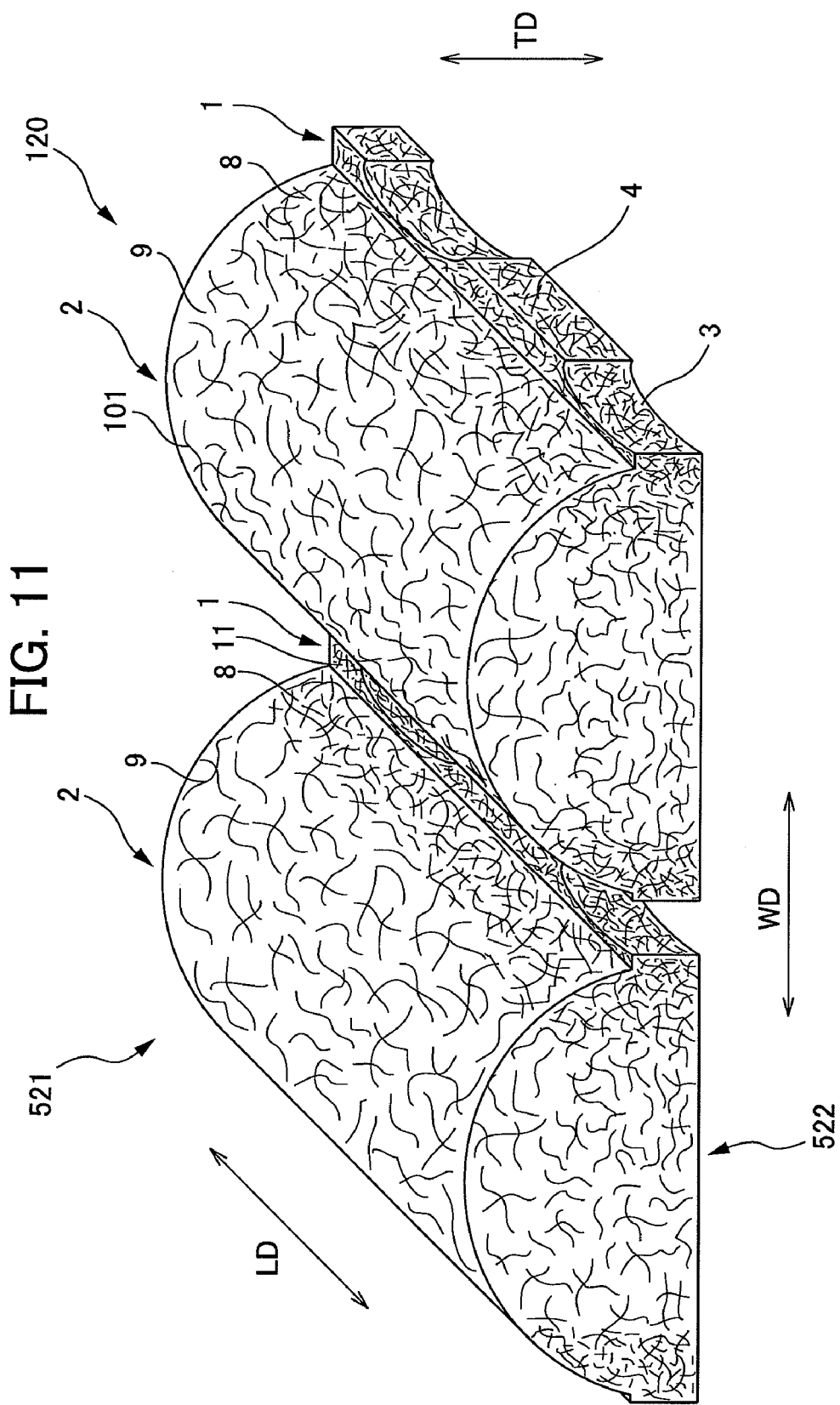
FIG. 11 shows an expanded perspective view of an area Y as described in FIG. 9.

FIG. 9 is a plan view showing a first surface 521 of nonwoven fabric according to the second embodiment, as used in a top sheet member 502 in the sanitary napkin as described in FIG. 1. FIG. 10 is a plan view of a second surface 522 opposite to the first surface 521 as described in FIG. 9. FIG. 11 is an expanded perspective view of a part showing a configuration of nonwoven fiber corresponding to the area demarcated with Y in FIG. 9. Suitably, the following will now explain FIGS. 9 to 11 with reference to FIGS. 1 and 2.

The top sheet member 502 is composed of the liquid-permeable nonwoven fabric 120 formed with gaps between fibers internally. Compared to the nonwoven fabric 110 described with the first embodiment above, the configuration of the nonwoven fabric 120 that compose the top sheet member 502 in that it includes a plurality of openings formed at predetermined gaps in the groove portions 1. In other words, the groove portions 1 which are an example of a concave portion, are provided between adjacent convex portions (a first convex portion 2 and a second convex portion 2) of the plurality of raised ridge portions 2, and include a plurality of openings 3 at predetermined intervals along the longitudinal direction LD. In addition, of the plurality of openings 3, a linking portion 4 is provided between the adjacent openings (a first opening 3 and a second opening 3) to link the convex portions (the first convex portion 2 and the second convex portion 2).

The fiber density of the side edge portions 8 of each of the plurality of raised ridge portions 2 in the thickness direction TD of the nonwoven fabric 120 is substantially uniform. The fiber density of the raised ridge portions 2 is higher than the average fiber density. The fiber density of the central portion 9, which is greater in height in the TD direction than the side edge portions 8 of each of the plurality of raised ridge portions 2, is substantially uniform in the thickness direction TD of the nonwoven fabric 120, and has a lower fiber density in the raised ridge portions 2 than the average fiber density.

In addition, compared to the linking portions 4, there are more longitudinally-orientated fibers (the first orientation fibers) having fibers orientated near the longitudinal direction LD, in the areas around each of the plurality of adjacent openings 3 in the side edge portions 8, and compared to the side edge portions 8, there are more laterally-orientated fibers (the second orientation fibers) having fibers orientated near the width direction WD, in the area around the plurality of adjacent openings 3 in the linking portions 4.

The actions and effects as the first embodiment are also attained with this configuration. In other words, menstrual blood that passes through the plurality of raised ridge portions 2 is readily transferred to the absorbent body member 503 without building up at the second surface 522. Particularly, the central areas 9 have a low fiber density, so a larger volume of menstrual blood can pass through this region compared to that of the side edge areas 8, and can be readily guided to the absorbent body member 503. In addition, although the fiber density is high at the side edge areas 8, the fibers have not been made into film, so the wearer does not have foreign-body sensation, or experience a poor feeling against the skin.

In addition, because a plurality of openings 3 are formed in the groove portions 1, it is well-suited to allowing fluids and solids to pass through. Furthermore, the fibers 101 at the bottom portion of the groove portions 1 are orientated in the width direction WD, so it is possible to prevent the liquid from flowing too far in the longitudinal direction LD of the groove portions 1 and spreading widely.

Furthermore, each of the side edge areas 8 of the plurality of raised ridge portions 2 has a higher fiber density than the central areas 9, and the rigidity of the fibers is increased. Therefore, the plurality of raised ridge portions 2 is supported by each of the side edge portions 8 making it difficult for raised ridge shapes to be crushed by external pressure. In addition, this also makes it possible to prevent the raised ridge portions 2 from being crushed under the weight of large volumes of bodily fluids.

Also, as described above, either longitudinally-orientated fibers (the first orientation fibers) or laterally-orientated fibers (the second orientation fibers) can be more prevalent in any location in the portions around each of the plurality of openings 3. Thus allowing the shape of the openings 3 to be more easily maintained.

2-2-1. Shape

The following will now explain in detail the shape of the nonwoven fabric 110 that is used in the top sheet member 502 with suitable reference to FIGS. 1, and 9 to 11. A first side of the fiber assembly is support by a supporting member having portions that allow a fluid, described below, to pass therethrough. When the fibers that compose the fiber assembly are in a state having a degree of freedom, the fibers of a portion of the fiber assembly are displaced by a fluid composed mainly of a gas being blown thereupon, so the plurality of the groove portions 1, the plurality of raised ridge portions 2 and the plurality of openings 3 included in the raised ridge portions 2 are formed in the nonwoven fabric 120.

The plurality of groove portions 1 are formed in parallel in the nonwoven fabric 120 at substantially equal distances along the longitudinal direction LD on the first surface 521 side of the nonwoven fabric 120, and the plurality of openings 3 are formed in the groove portions 1. Each of the plurality of openings 3 is substantially an elongated or substantially an oval-shaped hole. Other substantially circle-shaped configurations are conceivable. This embodiment describes that the groove portions 1 are formed in parallel at substantially equal intervals, however, is not limited to this. For example, the groove portions may be formed for each different interval, or formed so that intervals between the groove portions 1 are different. Also, the open portions 3 are formed at substantially equal intervals, however this should not be considered limiting and the open portion 3 may be formed at different intervals.

A detailed description of each of the shapes of the plurality of groove portions 1 and the plurality of raised ridge portions 2, excluding the openings 3, in the nonwoven fabric 120 is the same as the description for the nonwoven fabric 110 in the first embodiment. Therefore, an explanation will be omitted. (See section 1-2-1. Shapes) In the nonwoven fabric 120, between each of the plurality of open portions 3, the linking portions 4 are formed so as to connect the raised ridge portions 2 adjacent to the groove portions 1 with each other. In other words, the plurality of linking portions 4 formed at predetermined intervals connect the raised ridge portions 2 with the adjacent raised ridge portions 2.

Both of the length of the opening 3 in the longitudinal direction LD and the length in the width direction WD are 0.1 to 5 mm, preferably 0.5 to 4 mm as an example. Each of the pitches of the openings 3 adjacent to each other and across the linking portions 4 is 0.5 to 30 mm, preferably 1 to 10 mm as an example.

The height of each of the linking portions 4 in the thickness direction TD of the nonwoven fabric 120 is equal to or less than that of each of the raised ridge portions 2 in the thickness direction TD of the nonwoven fabric 120, preferably 20 to 100% and more preferably, 40 to 70% as an example.

The length of each of the linking portions 4 in the longitudinal direction LD of the nonwoven fabric 120 and the length in the width direction WD is 0.1 to 5 mm, preferably 0.5 to 4 mm as an example. Each of pitches between the tops of the linking portions 4 adjacent to each other and across the openings 3 is 0.5 to 30 mm, preferably 1 to 10 mm as an example.

The cross-sectional shape of each of the linking portions 4 in the longitudinal direction LD of the nonwoven fabric is formed into a substantially square shape. The cross-sectional shape of each of the joining portions 4 in the longitudinal direction is not limited to a substantially square shape. The shapes such as dome shapes, trapezoid shapes, triangular shapes and Ω-shapes are all possible. To prevent a predetermined liquid from spreading in the groove portions 1, a substantially square shape is preferable. Moreover, the top of the linking portion 4 is preferably flat or curved so as not to the linking portion 4 giving a foreign body sensation by touching the skin or the like under an excessive external pressure.

2-2-2. Fiber Orientation

The following will now explain the orientation of the fibers of the nonwoven fabric 120 that is used in the top sheet member 502 with suitable reference to FIGS. 1, and 9 to 11. A detailed description of each of the fiber orientations of the plurality of groove portions 1 and plurality of raised ridge portions 2, excluding the openings 3, in the nonwoven fabric 120 is the same as the description for the nonwoven fabric 110 in the first embodiment. Therefore, an explanation will be omitted. (See section 1-2-1. Shapes) The groove portions 1 are areas formed by being blown directly by fluid (such as hot air), and in which the openings 3 and linking portions 4 are formed. When fluid is blown onto the fibers 101, the portion being blown forms a channel in the thickness direction and at the same time, the longitudinally-orientated fibers orientated in the longitudinal direction LD in the portion blown by the fluid are displaced to the side edge portions 8. The laterally-orientated fibers orientated in the width direction WD by the fluid and the fluid, the direction of flow of which is modified by being blown against an air-impermeable supporting member, described below, are displaced towards the linking portions 4. Doing this orientates the fibers 101 in the linking portions 4 of the groove portions 1 in a direction perpendicular to the longitudinal direction LD of the groove portions 1. Specifically, the fibers are orientated overall in the width direction WD. Therefore, the fibers 101 around the outer edges of the openings 3 are arranged along the opening shape.

The percent content of the longitudinally-orientated fibers is lowest and the percent content of the laterally-orientated fibers is highest at the linking portions 4 of the groove portions 1 in the nonwoven fabric 120. The linking portions 4 of the groove portions 1 are formed to have a percent content of laterally-orientated fibers of 55% to 100%, and preferably 60% to 100%, in the same way as the nonwoven fabric 110 of the first embodiment.

2-2-3. Fiber Compression

As shown in FIGS. 9 to 11, the average fiber density is adjusted to be lower at the groove portions 1 than at the raised ridge portions 2. This adjustment of the fiber density is the same as was described in relation to the first embodiment. The fiber density of the raised ridge portions 2 can be freely adjusted by several conditions, such as the amount of blown fluid (for example hot air), and a web tension.

A fiber density of the linking portion 4 in the groove portion 1 is 0.005 to 0.20 g/cm$^3$, preferably, 0.007 to 0.10 g/cm$^3$ as an example. Where the fiber density of the linking portion 4 is less than 0.005 g/cm$^3$, the linking portion 4 as well may be crushed when the raised ridge portion 2 is crushed by an excessive external pressure.

On the other hand, where a fiber density of the linking portion 4 is greater than 0.20 g/cm$^3$, the predetermined liquid dropped onto the groove portion 1 will gather on the linking portion 4 and, if an excessive external pressure is applied to the nonwoven fabric 120 and the liquid comes into direct contact with the skin, a wet feeling may result. In addition, the nonwoven fabric 120 is formed so that the void area ratio measured from the first surface 521 of the nonwoven fabric 120 is lower than the void area ratio measured from the second surface 522 of the nonwoven fabric 120. Here, the void area ratio is the proportion of void area where no fibers exist versus the overall area. The void area ratio is measured using the following method.

Following is an outline of the method used to measure percent open area with a digital microscope VHX-100 made by Keyence Corporation. First, (1) set a sample on the measuring instrument so that the direction along the groove portion 1 and the raised ridge portion 2 is in a longitudinal direction on a bench, and (2) in the top of the raised ridge portion 2, make the following measurement from a projecting surface of the raised ridge portion 2 and a surface on the opposite side to the projecting surface, respectively.

(3) Set the lens magnification of the measuring instrument and the magnification on a personal computer screen to an appropriate level and then focus the lens on the nearest fiber of the sample, excluding fibers that irregularly project to the front. (4) Define an appropriate shooting depth and prepare a 3D image of the sample.

(5) Convert the 3D image into 2D image to allow 2D processing to defined the volume and identify the space between fibers within the specified range. Furthermore, (6) the 2D image is converted into a binary image where the area occupied by fibers is converted into white and the area not occupied by fibers is converted into black. Then (7) reverse the color to turn the area not occupied by fibers into white, and measure the white area.
With a magnification of 300 times and a shooting depth of 220 μm (one shot at every 20 μm, a total of 11 shots), make measurements (n=10) and take an average value.
The percent open area is calculated from the following formula:

Percent open area(%)=(total of open area (mm$^2$)/Measured area (mm$^2$)×100)

The total of open area can be calculated from (Total of open area at measurement/Enlargement magnification at measurement), and the measured area can be calculated from (Measured area at measurement/Enlargement magnification at measurement).

The fact that the fiber-to-fiber distance becomes greater and the surface of the fabric becomes rougher as the percent open area increases indicates that the fiber 101 is able to move, thus attaining a high degree of freedom. Furthermore, since the open area per unit area is high relative to nonwoven fabric having a greater fiber-to-fiber distance partially by means of opening processing or the like, the fiber-to-fiber distance increases in the whole surface to which fluid mainly composed of gas in the nonwoven fabric blows. Therefore, for example, in using the nonwoven fabric for an absorbable product, the resistance when a predetermined liquid, such as an excretory substance, passes through the nonwoven fabric 120 can be reduced, thus facilitating movement of the liquid into an absorber or the like.

The open area per unit area refers to a percentage of the total area without fiber to the number of spaces without fiber within a predetermined area. The open area can be calculated as follows:

Open area (mm$^2$/pc)=(Total of open area (mm$^2$)/Number of open areas(pc))

A difference between a percent open area measured from a face on the side where the raised ridge portion 2 protrudes outward in the raised ridge portion 2 and a percent open area measured from a face on the opposite side to the face on the side where the raised ridge portion 2 protrudes is 5 to 100%, preferably 5 to 80%, more preferably, 15 to 40% as an example.

The percent open area measured from the face on the side where the raised ridge portion 2 protrudes is 50 to 100%, preferably, 50 to 90%, further preferably, 50 to 80%.

Further, the open area per unit area measured from the face on the side where the raised ridge portion 2 protrudes is greater than 3000 μm$^2$, preferably, 3000 to 30000 μm$^2$ and more preferably 5000 to 20000 μm$^2$.

2-2-4. Basis Weight

The average basis weight of the fibers of the overall nonwoven fabric 120 is the same as the average basis weight of the fibers of the overall nonwoven fabric 110 in the first embodiment. In addition, the relationship of the average basis weights of the raised ridge portions 2 and groove portions 1 is the same as that of the nonwoven fabric 110 in the first embodiment. (See section 1-2-4. Basis Weight)

A basis weight of the linking portion 4 is 5 to 200 g/m$^2$, preferably, 10 to 100 g/m$^2$ as an example. With the basis weight of the linking portion 4 of less than 5 g/m$^2$, the linking portion 4 as well may be crushed when the raised ridge portion 2 is crushed by excessive external pressure. Where the basis weight of the linking portion 4 is more than 200 g/m$^2$, the predetermined liquid dropped onto the groove portion 1 will accumulate in the region of the linking portion 4 and, if an excessive external pressure is applied to the nonwoven fabric 120, the fluid will make direct contact with the skin, thus a wet feeling may be result.

2-2-5. Others

The same effects as the sanitary napkin 501 that uses the nonwoven fabric 110 of the first embodiment as the top sheet member are attained even in a sanitary napkin that uses the nonwoven fabric 120 of the second embodiment as the top sheet member. (See section 1-2-5. Others) Particularly, because a plurality of openings 3 are formed in the groove portions 1, they allow liquid or solids (fine particles and the like) to pass through. The openings 3 and linking portions 4 orientated in the width direction WD prevent liquid from spreading widely by flowing to far in the longitudinal direction LD of the groove portions 1.

2-2-6. Manufacturing Method

Figure 12:
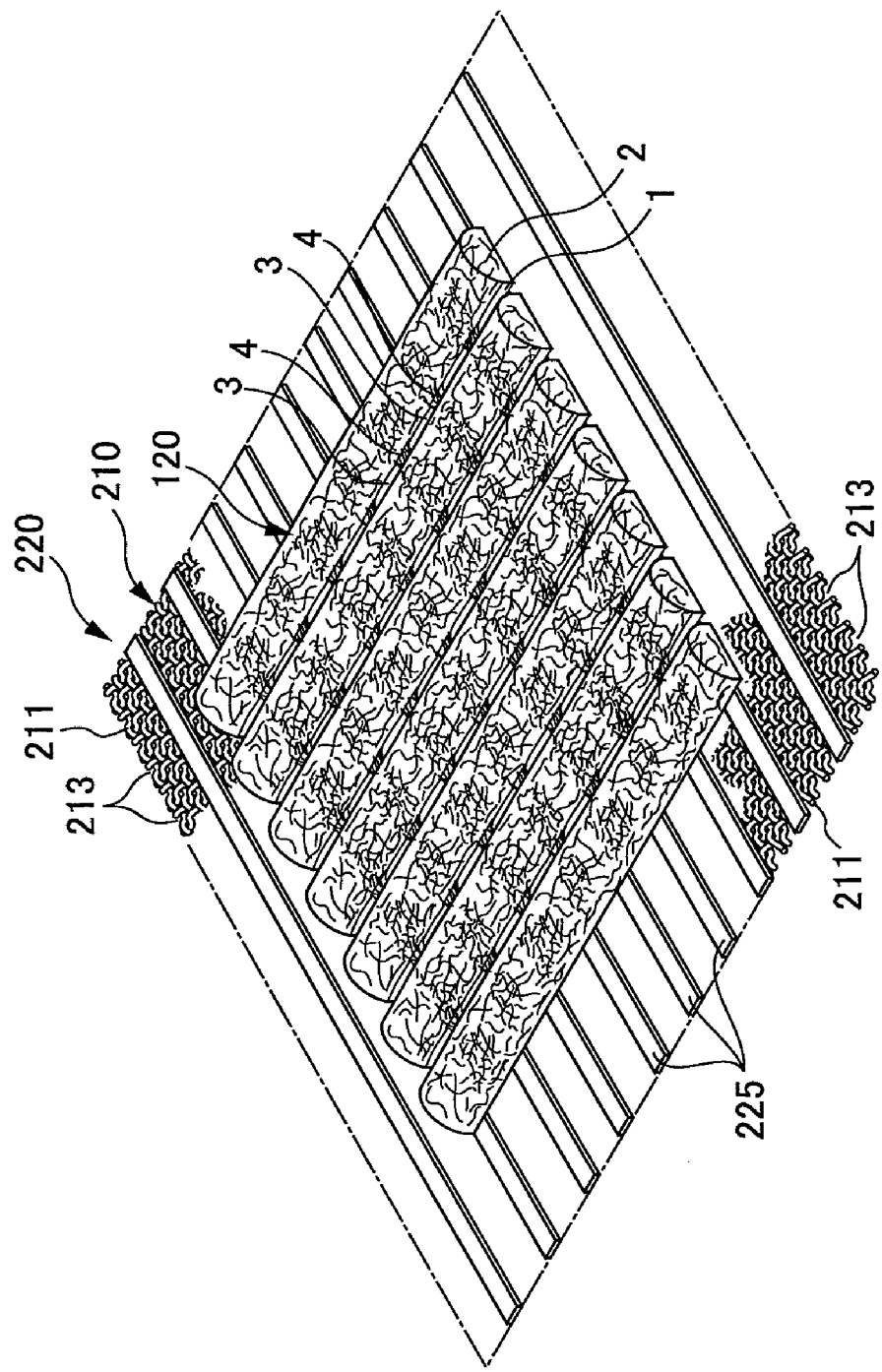
FIG. 12 shows nonwoven fabric as described in FIGS. 9 to 11 supported by an air-permeable supporting member being manufactured.

FIG. 12 shows the fiber web blown by a gas from above, the fiber web being supported by an air-permeable supporting member as described in FIG. 6, and is a view of the nonwoven fabric as shown in FIGS. 9 to 11 being manufactured. The method for manufacturing the nonwoven fabric 120 of this embodiment will be explained below with suitable reference to FIGS. 6 and 8. First, the fiber web 100 is placed on a top surface side of the supporting member 220, which is an air-permeable supporting member. Said another way, the fiber web 100 is supported from a bottom side (second surface second surface 522) by the supporting member 220.

As described in relation to the first embodiment, using the mechanism of FIG. 8, the supporting member 220 in a state supporting the fiber web 100 as described in FIG. 6 is used as the air-permeable supporting member 200. In other words, it is possible to manufacture the nonwoven fabric 120 by continuously blowing a gas from the top surface side of the fiber web 100 while moving the supporting member 220 in predetermined direction (F).

The supporting member 220 described above is equipped with air ventilation portions that allow the fluid blown from the top surface side (first surface 521 side) of the fiber web 100 as described in FIG. 6 to ventilate to an underside that is the opposite side to the side where the fiber web 100 is disposed on the supporting member 220; and air-impermeable portions that do not allow the fluid blow from the top surface side of the fiber web 100 to ventilate to an underside of the supporting member 220, and do not allow the fibers 101 that compose the fiber web 100 to move to the opposite side of the supporting member 220.

The air-permeable portions are mesh holes 213 (see FIG. 12) of a predetermined mesh supporting member 210. An example of air-impermeable portions can be a configuration that disposes rod-shaped members 225 that are air-impermeable in parallel at predetermined intervals in the mesh supporting member 210. The shapes and arrangements of the air-impermeable rod-shaped members 225 can be changed as required. Also, the shapes of the air-impermeable portions can be changed by filling in the holes 213 in the air-permeable mesh supporting member 210 (such as by using solder or resin).

A ventilation degree in an area as a permeable portion is, for example, 10,000 to 60,000 cc/cm$^2$·min, preferably, 20,000 to 50,000 cc/cm$^2$·min as an example. However, a ventilation degree greater than a value described above may sometimes occurs in such a case where a permeable portion is formed, for example, by cutting out a metal plate or the like because the resistance of fluid, mainly composed of gas, to the plate portion becomes lost.

The mesh supporting member 210 constituting the supporting member 220 and the slender members 225 control movement of the fiber 101 to downside of the supporting member 220, so that the fiber 101 is moved in such a direction along the top of the supporting member 220. Specifically, the gas blown onto the slender members 225 is redirected to such a direction along the slender members 225. The gas which has been redirected moves the fiber 101 disposed on the tops of the mesh members 225 to a surrounding area from the tops of the slender members 225. This process forms the open portion 3 of a predetermined shape. At least one of orientation, fiber density or basis weight of the fiber 101 is adjusted.

To form the nonwoven fabric 120 with the openings 3, a supporting member different from the supporting member 220 described above may be used. The size or arrangement of the like of the groove portion 1, the raised ridge portion 2, the opening 3 and linking portion 4 may be changed with the supporting member.

3. Evaluation of Absorption Performance

Artificial blood was used to measure infiltration speed to the top sheet member, drying speed, low residual amounts of liquid, and spreading area to evaluate performance to suppress final liquid return. A sanitary napkin that adopted the nonwoven fabric 120 of the second embodiment was used as the top sheet. Also, two types of conventional sanitary napkins were also used for the same evaluations to be used for comparison. Note that the absorbent bodies covered by the top sheet in each sanitary napkin used for evaluation and for comparison had substantially the same performance.

3-1. Overview of the Method of Evaluation

A suitable amount of artificial blood was repeatedly applied to each sanitary napkin used for evaluation and for comparison. This was done to measure the time it takes for the artificial blood to permeate the top sheet, for each drop, to evaluate the liquid infiltration speed and drying speed. Also, by measuring the thermal migration speed $Q_{max}$ of the top surface of the top sheet, the low residual amounts of liquid of the top sheet was evaluated. Also, by measuring the thermal migration speed $Q_{max}$ of the top surface of the top sheet, the low residual amounts of liquid of the top sheet was evaluated.

3-2. Measuring Instruments

The following measuring instruments were assembled to use in the evaluation method described above. A scale; a ruler; artificial blood; a Metrohm Corporation made auto burette 725 type; n acrylic plate with a hole (40 mm×10 mm hole; length×width=200 mm×100 mm; weight: 126 g); a Kato Tech Corporation made Finger Robot Thermo Lab KES-F7; filter paper (length×width=50 mm×35 mm; 10 sheets to a set; measured in advance as weight A [g]); an acrylic plate (length×width=200 mm×100 mm; weight 130 g), and a weight (combined with the acrylic plate, 50 g/cm² per unit surface area of the size of the filter paper).

3-3. Evaluation Procedures

For evaluations, five of each of the sanitary napkins for comparison were prepared. In each of the same type of sanitary napkin, measurements relating to the series of evaluation procedures shown below from 1) to 9-b), using the measuring instruments described in section 6-2, were performed five times, and the average was evaluated.

1) The acrylic plate with a hole was laid so that the hole would be at any central region of the top sheet of the prepared sanitary napkin. 2) The nozzle of the auto burette was positioned 10 mm above the acrylic plate with a hole.

3-a) Artificial blood was applied for the first time through the hole in the acrylic plate onto the exposed top sheet (Application rate: 95 ml/min; Quantity: 3 ml). 3-b) Then, immediately after the artificial blood was applied, the time (infiltration speed) for the artificial blood accumulated in the hole of the acrylic plate to permeate the top sheet surface was measured. 3-c) Time measurement commenced immediately after the artificial blood begins permeating the top sheet surface to measure the time (drying speed) until it is determined that the artificial blood has completed permeation from the top sheet to the lower absorbent body. Note that if the artificial blood does not permeate within 60 seconds, then it is determined that the top sheet did not dry. 3-d) The acrylic plate with the hole was removed from the top sheet.

4-a) One minute after the application has been completed, the KES-F7 was used to measure (thermal migration $Q_{max}$) the residual liquid on the outermost surface of the top sheet. 4-b) A ruler was used to measure the range of spreading (spreading range) of the artificial blood in the uppermost surface of the top sheet. 4-c) The acrylic plate with a hole was placed on top of the top sheet again, in the same way as was described for 1) above (This is to prepare for applying the artificial blood a second time.)

5-a) 1.5 minutes after the first application of the artificial blood was completed, the second artificial blood application commenced, in the same way as was described in 3-a) above (Application rate: 95 ml/min; Quantity: 4 ml). 5-b) Measurements were taken again for the infiltration speed, in the same way as was described at 3-b) above. 5-c) Measurements were taken again for the drying speed, in the same way as was described at 3-c) above. 5-d) The acrylic plate with a hole was then removed, in the same way as was described at 3-d) above.

6-a) Measurements were taken again for the $Q_{max}$, in the same way as was described at 4-a) above. 6-b) Measurements were taken again for the spreading area, in the same way as was described at 4-b) above. 6-c) The acrylic plate with a hole was placed on top of the top sheet again, in the same way as was described for 1) above (This was to prepare for the application the artificial blood for a third time).

7-a) 1.5 minutes after the second application of the artificial blood was completed, the third artificial blood drop commenced, in the same way as was described at 3-a) above. (Application rate: 95 ml/min; Quantity: 3 ml). 7-b) Measurements were taken again for the infiltration speed, in the same way as was described at 3-b) above. 7-c) Measurements were taken again for the drying speed, in the same way as was described at 3-c) above. 7-d) The acrylic plate with a hole was removed, in the same way as was described at 3-d) above.

8-a) Measurements were taken again for the $Q_{max}$, in the same way as was described at 4-a) above. 8-b) Measurements were taken again for the spreading area, in the same way as was described at 4-b) above.

9-a) 1.5 minutes after the third application of the artificial blood was completed, ten sheets of filter paper were positioned at any central region of the top sheet, and the acrylic plate was placed on the ten sheets of filter paper. The weight was then placed on the acrylic plate. 9-b) This was left to stand for one minute in the state described at 9-a), then the weight and the acrylic plate were removed to measure the weight B [g] of the filter paper. The value of B [g] was subtracted (rewetting amount) from the weight A [g] of the filter paper prior to use to measure the rewetting amount per 10 ml of artificial blood to evaluate the suppression performance of liquid return.

$$\text{Rewetting rate }(\%)=\{(B-A)\text{ g}/10\text{ ml}\}\times 100$$

The measurements and calculations relating to the series of evaluation procedures from 1) to 9-b) were conducted five times on the sanitary napkins for evaluation for comparison and evaluation. FIG. 13 shows the results of the averages attained (evaluations) (See the ave column). The sanitary napkins of this embodiment used for evaluation were the sanitary napkins that adopted the configuration of the nonwoven fabric 120 of the second embodiment as described above. Compared to the conventional sanitary napkin 1, and 2 that were used for comparison, the sanitary napkin of the present embodiment attained significantly superior results in rewetting amounts (0.27 g) and rewetting rates (2.7%) that were used to evaluate liquid return suppression performance, and attained high evaluations.

Also, though not shown, at 9-a) instead of the filter paper and acrylic plate, artificial leather was placed under 50 g/cm² of pressure and left for 1.5 minutes. Then, the rewet area was evaluated by binarization of the traces of artificial blood transferred from the artificial leather to the artificial skin, for the filter paper. While in the evaluation of the rewetting area, the sanitary napkin of the present embodiment was 350 to 400 mm², the comparison examples of 1 and 2 were at 1,300 to 1,450 mm². It can be said that the sanitary napkin of the embodiment is markedly superior.

The evaluation above was conducted using a sanitary napkin that adopted the configuration of the nonwoven fabric 120 of the second embodiment, but superior evaluation results can be attained compared to the sanitary napkin used for comparison and evaluation even if sanitary napkins that adopted the configuration of the nonwoven fabric 110 of the first embodiment.

In view of the above evaluations, the superior effects of liquid infiltration performance and liquid return suppression performance is attained by implementing the nonwoven fabric (120, 110 or the like) of the present invention in a top sheet member 502 that is used on a skin-contact surface of a sanitary napkin, if the absorbent article of the present invention is used. In other words, the first surface 521 side (skin side) of the top sheet member 502 as well as the second surface 522 side (the side in contact with the absorbent body) make it difficult for the liquid to build up, and enable liquid to travel quickly to the absorbent body side. In other words, the structure makes it difficult for the raised ridge portions to be crushed even if applied with an external pressure, so the wearer's skin is not soiled, and can alleviate a sticky feeling, regardless of changes in the wearer's activity or volume of menstrual blood.

4. Third Embodiment

Figure 14:
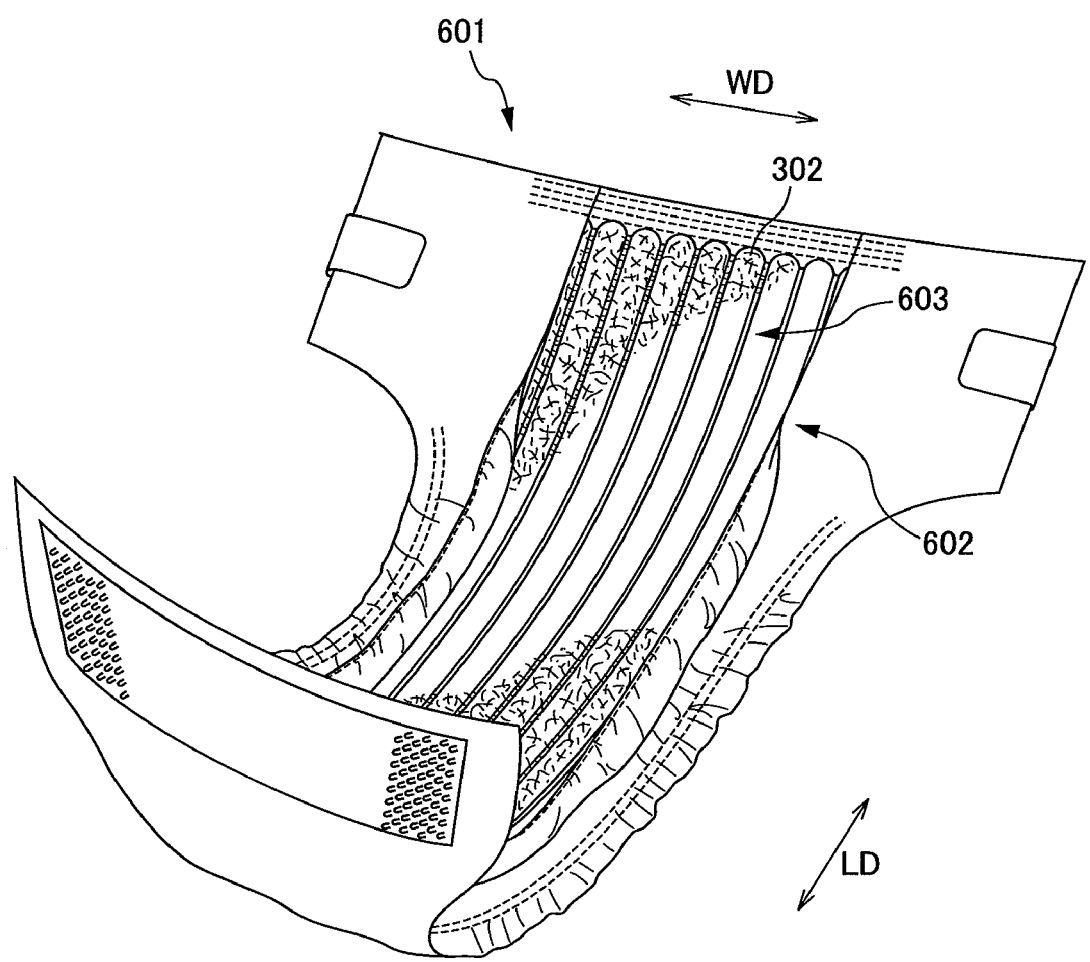
FIG. 14 is a composition drawing showing a disposable diaper as an absorbent article according to a third embodiment.

FIG. 14 is a composition drawing showing a disposable diaper as an absorbent article according to the present invention. A nonwoven fabric 302 that is the same as the nonwoven fabric 110 of the first embodiment is used as the top sheet of a disposable diaper 601 as the third embodiment in the absorbent member 602. The same nonwoven fabric as others or the nonwoven fabric 120 of the second embodiment can be used in the nonwoven fabric 302. Furthermore, the disposable diapers 601 can be expected to have the same actions and effects as the articles described above.

As explained above, according to the present invention, nonwoven fabric used as a top sheet (the surface sheet) and having concavity and convexity significantly improve liquid infiltration performance and liquid return suppression performance, provide high strength and do not worsen the feeling against the skin. This makes it possible to provide an absorbent article that can respond to high performance requests. Particularly, it is possible to provide an absorbent article that does not soil the skin, and dramatically alleviates a sticky feeling if menstrual blood is repeated excreted, or pressure is applied to contact the skin, such as in a sitting posture, or there are changes in activity.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent article, comprising:
   a first sheet member that is liquid-permeable;
   a second sheet member that is liquid-impermeable; and
   an absorbent member that absorbs and retains liquid, disposed between the first and second sheet members,
   wherein at least a portion of the first sheet member comprises nonwoven fabric having a plurality of convex and concave portions extending in a first direction of the nonwoven fabric, wherein said convex and concave portions are alternatively arranged in a second direction perpendicular to the first direction, and a fiber density of entire each convex portion is greater than that of entire each concave portion,
   wherein each of said convex portions has side edge areas and a central area between said side edge areas,
   wherein
   a fiber density of each of said side edge areas and central areas is substantially uniform in a thickness direction of the nonwoven fabric, respectively,
   a fiber density of each of said side edge areas is greater than that of each of the central areas, and
   a dimension of each of the convex portions in the second direction is greater than that of each of the concave portions.

2. The absorbent article according to claim 1, wherein the nonwoven fabric further comprises:
   first orientation fibers orientated along the first direction; and
   second orientation fibers orientated along the second direction;
   wherein the side edge areas in each of the convex portions have more first orientation fibers than the central area in said convex portion.

3. The absorbent article according to claim 2, wherein each said concave portion includes
   a plurality of openings formed at predetermined intervals along the first direction; and
   linking portions arranged between the adjacent openings and linking the side edge areas of the convex portions on opposite sides of said concave portion,
   wherein each of said linking portions has more second orientation fibers than the linked side edge areas.

4. The absorbent article according to claim 3, wherein said nonwoven fabric along a peripheral edge of each said opening includes
   first portions adjacent to the side edge areas of the convex portions on the opposite sides of said concave portion and having more first orientated fibers than the linking portions, and
   second portions adjacent to the linking portions and having more second orientation fibers than the side edge areas.

5. The absorbent article according to claim 1, wherein the central area has more fibers obliquely orientated in the thickness direction than the side edge areas in each of the convex portions.

6. The absorbent article according to claim 2, wherein the central area has more fibers obliquely orientated in the thickness direction than the side edge areas in each of the convex portions.

7. The absorbent article according to claim 3, wherein the central area has more fibers obliquely orientated in the thickness direction than the side edge areas in each of the convex portions.

8. The absorbent article according to claim 4, wherein the central area has more fibers obliquely orientated in the thickness direction than the side edge areas in each of the convex portions.

9. The absorbent article according to claim 1, wherein a basis weight of fibers forming a bottom portion of each of the concave portions is lower than that of fibers forming the central area of each of the convex portions.

10. The absorbent article according to claim 2, wherein a basis weight of fibers forming a bottom portion of each of the concave portions is lower than that of fibers forming the central area of each of the convex portions.

11. The absorbent article according to claim 3, wherein a basis weight of fibers forming a bottom portion of each of the concave portions is lower than that of fibers forming the central area of each of the convex portions.

12. The absorbent article according to claim 4, wherein a basis weight of fibers forming a bottom portion of each of the concave portions is lower than that of fibers forming the central area of each of the convex portions.

13. The absorbent article according to claim 5, wherein a basis weight of fibers forming a bottom portion of each of the concave portions is lower than that of fibers forming the central area of each of the convex portions.

14. The absorbent article according to claim 2, wherein a bottom portion of each of the concave portions has more second orientation fibers than the central area of each of the convex portions.

15. The absorbent article according to claim 3, wherein a bottom portion of each of the concave portions has more second orientation fibers than the fibers forming the central area of each of the convex portions.

16. The absorbent article according to claim 4, wherein a bottom portion of each of the concave portions has more second orientation fibers than the central area of each of the convex portions.

17. The absorbent article according to claim 6, wherein a bottom portion of each of the concave portions has more second orientation fibers than the central area of each of the convex portions.

18. The absorbent article according to claim 7, wherein a bottom portion of each of the concave portions has more second orientation fibers than the central area of each of the convex portions.

19. The absorbent article according to claim 1, being manufactured by a method comprising:
supporting a first side of a fiber assembly on a supporting member that has portions allowing a fluid to pass through said portions;
conveying said fiber assembly supported by the supporting member in a machine direction; and
blowing the fluid onto an opposite, second side of the fiber assembly, which is being conveyed in the machine direction in the conveying step, to form said convex and concave portions.

20. An absorbent article, comprising:
a first sheet member that is liquid-permeable;
a second sheet member that is liquid-impermeable; and
an absorbent member that absorbs and retains liquid, disposed between the first and second sheet members,
wherein at least a portion of the first sheet member comprises nonwoven fabric having a plurality of convex and concave portions extending in a first direction of the nonwoven fabric, wherein said convex and concave portions are alternatively arranged in a second direction perpendicular to the first direction,
wherein each of said convex portions has side edge areas and a central area between said side edge areas,
wherein
a fiber density of each of said side edge areas and central areas is substantially uniform in a thickness direction of the nonwoven fabric, respectively,
a fiber density of each of said side edge areas is greater than that of each of the central areas,
a dimension of each of said convex portions in the second direction is greater than that of each of said concave portions, and
the nonwoven fabric further comprises:
first orientation fibers orientated along the first direction; and
second orientation fibers orientated along the second direction;
wherein the side edge areas in each of the convex portions have more first orientation fibers than the central area in said convex portion.

* * * * *